US008852106B2

(12) United States Patent
Kasahara et al.

(10) Patent No.: US 8,852,106 B2
(45) Date of Patent: Oct. 7, 2014

(54) ULTRASOUND DIAGNOSTIC APPARATUS

(75) Inventors: Eiji Kasahara, Mitaka (JP); Masaru Murashita, Mitaka (JP)

(73) Assignee: Hitachi Aloka Medical, Ltd., Tokyo (JP)

( * ) Notice: Subject to any disclaimer, the term of this patent is extended or adjusted under 35 U.S.C. 154(b) by 153 days.

(21) Appl. No.: 12/755,045

(22) Filed: Apr. 6, 2010

(65) Prior Publication Data
US 2010/0262006 A1 Oct. 14, 2010

(30) Foreign Application Priority Data

| Apr. 13, 2009 | (JP) | 2009-096817 |
| Sep. 14, 2009 | (JP) | 2009-211577 |
| Sep. 18, 2009 | (JP) | 2009-216854 |
| Jan. 7, 2010 | (JP) | 2010-001867 |
| Feb. 2, 2010 | (JP) | 2010-020940 |

(51) Int. Cl.
*A61B 8/00* (2006.01)
*A61B 5/02* (2006.01)
*A61B 8/08* (2006.01)
*A61B 5/00* (2006.01)
*A61B 6/00* (2006.01)
*G01S 15/89* (2006.01)
*A61B 8/02* (2006.01)
*G01S 7/52* (2006.01)

(52) U.S. Cl.
CPC .............. *A61B 8/0866* (2013.01); *A61B 5/7289* (2013.01); *G01S 7/52065* (2013.01); *G01S 7/52088* (2013.01); *A61B 6/5288* (2013.01); *G01S 15/8979* (2013.01); *A61B 8/02* (2013.01); *G01S 15/8993* (2013.01); *G01S 7/52085* (2013.01)
USPC ........................................ 600/443

(58) Field of Classification Search
USPC .......................................... 600/443
See application file for complete search history.

(56) References Cited

U.S. PATENT DOCUMENTS 5,099,847 A 3/1992 Powers et al.
5,159,931 A 11/1992 Pini
(Continued)

FOREIGN PATENT DOCUMENTS

EP 1 967 867 A2 9/2008
JP 4-99566 A 3/1992
(Continued)

OTHER PUBLICATIONS

"Dev Maulik," "Four-Dimensional B-Mode and Color Doppler Echocardiography of the Human Fetus," Doppler ultrasound in Obstetrics and Gynecology, chapter 34 pp. 509-516, 2005.*

(Continued)

*Primary Examiner* — Tse Chen
*Assistant Examiner* — Patricia Park
(74) *Attorney, Agent, or Firm* — Westerman, Hattori, Daniels & Adrian, LLP

(57) ABSTRACT

A pre-memory 14 stores a plurality of sets of tomographic image data in a time-series order. A virtual period setting unit 22 calculates a virtual period relating to an object based on the tomographic image data stored in the pre-memory 14. A base image searching unit 24 searches for base images from the tomographic image data using the virtual period. A division basis setting unit 26 sets division bases according to the base images within an image string constituted of tomographic image data. A reconfiguration processing unit 20 uses the respective base images as boundaries for the division to divide the tomographic image data stored in the pre-memory 14 into a plurality of image groups. Then, data blocks of tomographic images which correspond to one another on a periodic basis are sequentially extracted from the respective image groups, and are stored in a post-memory 28.

26 Claims, 14 Drawing Sheets

(56) References Cited

U.S. PATENT DOCUMENTS

| | | |
|---|---|---|
| 5,551,434 A | 9/1996 | Iinuma |
| 5,570,430 A | 10/1996 | Sheehan et al. |
| 5,766,129 A | 6/1998 | Mochizuki |
| 5,976,088 A | 11/1999 | Urbano et al. |
| 6,139,500 A | 10/2000 | Clark |
| 6,190,321 B1 | 2/2001 | Pang et al. |
| 6,450,962 B1 | 9/2002 | Brandl et al. |
| 6,558,325 B1 | 5/2003 | Pang et al. |
| 6,638,225 B2 | 10/2003 | Kamiyama |
| 6,647,135 B2 | 11/2003 | Bonnefous |
| 6,673,017 B1 | 1/2004 | Jackson |
| 6,730,032 B2 | 5/2004 | Yamauchi |
| 6,780,152 B2 | 8/2004 | Ustuner et al. |
| 6,966,878 B2* | 11/2005 | Schoisswohl et al. ........ 600/443 |
| 6,980,844 B2 | 12/2005 | Schoisswohl |
| 7,006,862 B2* | 2/2006 | Kaufman et al. ............. 600/523 |
| 7,131,947 B2 | 11/2006 | Demers |
| 7,628,755 B2 | 12/2009 | Kim et al. |
| 2005/0049502 A1 | 3/2005 | Schoisswohl |
| 2005/0049503 A1 | 3/2005 | Schoisswohl et al. |
| 2005/0259864 A1* | 11/2005 | Dickinson et al. ............ 382/154 |
| 2006/0100515 A1 | 5/2006 | Nakata |
| 2006/0241457 A1 | 10/2006 | Nadadur et al. |
| 2007/0053566 A1 | 3/2007 | Kim et al. |
| 2008/0009735 A1 | 1/2008 | Murashita |
| 2008/0221450 A1 | 9/2008 | Kim et al. |
| 2008/0267482 A1 | 10/2008 | Abe et al. |
| 2008/0300486 A1 | 12/2008 | Tirumalai et al. |
| 2010/0168573 A1 | 7/2010 | Sherrill |

FOREIGN PATENT DOCUMENTS

| | | | |
|---|---|---|---|
| JP | 7-299072 A | 11/1995 | |
| JP | 9-327458 A | 12/1997 | |
| JP | 11-327 A | 1/1999 | |
| JP | 3537594 B2 | 6/2004 | |
| JP | 2005-74225 A | 3/2005 | |
| JP | 2006-116149 A | 5/2006 | |
| JP | 2006-167267 A | 6/2006 | |
| JP | 2007-054635 A | 3/2007 | |
| JP | 2008-142362 A | 6/2008 | |
| JP | 2008-264314 A | 11/2008 | |
| JP | 2008-295859 A | 12/2008 | |
| JP | 2008-543481 A | 12/2008 | |
| JP | 2009-119250 A | 6/2009 | |
| WO | 2006/136988 A2 | 12/2006 | |
| WO | WO 2006/136988 * | 12/2006 | ............... A61B 8/14 |
| WO | 2008-094218 A1 | 8/2008 | |

OTHER PUBLICATIONS

Brekke, S. et al.; "Dynamic 3D ultrasonic imaging of the fetal heart"; 2002 IEEE Ultrasonic Symposium, pp. 1593-1596.

Nelson, Thomas R. et al.; Three-Dimensional Echocardiographic Evaluation of Fetal Heart Anatomy and Function: Acquisition, Analysis and Display; 1996 by the American Institute of Ultrasound in Medicine, J Ultrasound Med, vol. 15, pp. 1-9.

Sklansky, Mark S., MD et al.; "Three-Dimensional Fetal Echocadiography: Gated Versus Nongated Techniques"; 1998 by the American Institute of Ultrasound in Medicine, J Ultrasound Med, vol. 17, pp. 451-457.

Sklansky, Mark S., MD et al.; "Real-Time Three-Dimensional Fetal Echocardiography: Initial Feasibility Study"; 1999 by the American Institute of Ultrasound in Medicine. J Ultrasound Med, vol. 18, pp. 745-752.

Extended European Search Report dated Sep. 19, 2012, issued in corresponding European Patent Application No. 10003745.6 (8 pages).

Office Action dated Feb. 4, 2013 issued in Chinese Patent Application No. 201010148456.4. English Translation.

Japanese Office Action dated Nov. 5, 2013, issued in corresponding Japanese Patent Application No. 2010-020940, w/ English translation.

Office Action dated Jun. 18, 2013 issued in corresponding Japanese Application No. 2009-096817, with English Translation. 6 pages.

European Office Action dated May 15, 2013, issued in corresponding European Patent Application No. 10003745.6 (7 pages).

Japanese Office Action dated Aug. 27, 2013, issued in corresponding Japanese Patent Application No. 2009-211577 with partial translation (4 pages).

Japanese Office Action dated Feb. 4, 2014, issued in corresponding Japanese Application No. 2010-020940 with English Translation. (6 pages).

* cited by examiner

ULTRASOUND DIAGNOSTIC APPARATUS

BACKGROUND

1. Technical Field

The present invention relates to an ultrasound diagnostic apparatus for forming display images of an object in periodic motion.

2. Related Art

Ultrasound diagnostic apparatuses for forming three-dimensional ultrasound images of tissue in motion, such as a heart, have been known. For example, in a known technique, ultrasonic beams are scanned in a three-dimensional region to acquire echo data, and, based on the acquired echo data, a three-dimensional ultrasound image is formed, to be displayed in real time. However, real-time display has a fundamental constraint in that a tradeoff relationship exists among the scan rate, the beam density, and the beam range.

A technique for preventing the fundamental constraint in the real-time display of three-dimensional ultrasound images has also been proposed. For example, JP 3537594B (Patent Document 1) discloses a technique in which a scanning plane is gradually displaced within the three-dimensional region in synchronization with electrocardiographic signals or the like; a plurality of sets of tomographic image data are acquired over a plurality of time phases at respective positions of the scanning planes; and the acquired tomographic image data are reconstructed to form three-dimensional image data (reconfiguration process or reconstruction process). However, difficulty is encountered in applying this technique to, for example, a fetus, from which electrocardiographic signals may not be obtained directly.

JP 2005-74225 A (Patent Document 2) discloses a technique for reconstruction by performing scanning at certain time intervals, rather than using electrocardiographic signals. However, in this technique, the motion period of a heart during data acquisition is assumed to be constant. If the motion period of a heart is not constant, the form of the heart in the reconstructed image may be distorted from the actual heart, thereby lowering reliability.

In view of the above-described background art, the inventor of the present invention has performed research and development for a technique of forming ultrasound images by means of a reconfiguration process. In particular, the inventor focused attention on the technique of forming ultrasound images of an object in unstable periodic motion, such as the heart of a fetus.

SUMMARY

The present invention has been conceived through the above-described research and development, and an object of the present invention is to improve the reliability of display images of an object in unstable periodic motion.

In order to achieve the object, an ultrasound diagnostic apparatus according to an aspect of the present invention includes a probe that emits and receives ultrasonic waves to and from a three-dimensional region including an object in periodic motion; an emission and reception controlling unit that controls the probe such that a scanning plane is displaced over a plurality of periods of the motion so as to form a plurality of scanning planes within the three-dimensional region; a base image searching unit that searches for a plurality of base images from an image string constituted of a plurality of images corresponding to the plurality of scanning planes according to a feature amount relating to the periodicity of the motion; an image reconfiguration unit that divides the image string into a plurality of image groups using the respective base images as dividing units, and extracts a plurality of images which correspond to one another on a periodic basis from the respective image groups; and a display image forming unit that forms a display image of the object based on the plurality of images which correspond to one another on a periodic basis.

According to this aspect, it is possible to improve the reliability of a display image of an object in unstable periodic motion.

DETAILED DESCRIPTION

Hereinafter, a preferred embodiment of the present invention will be described.

Figure 1:
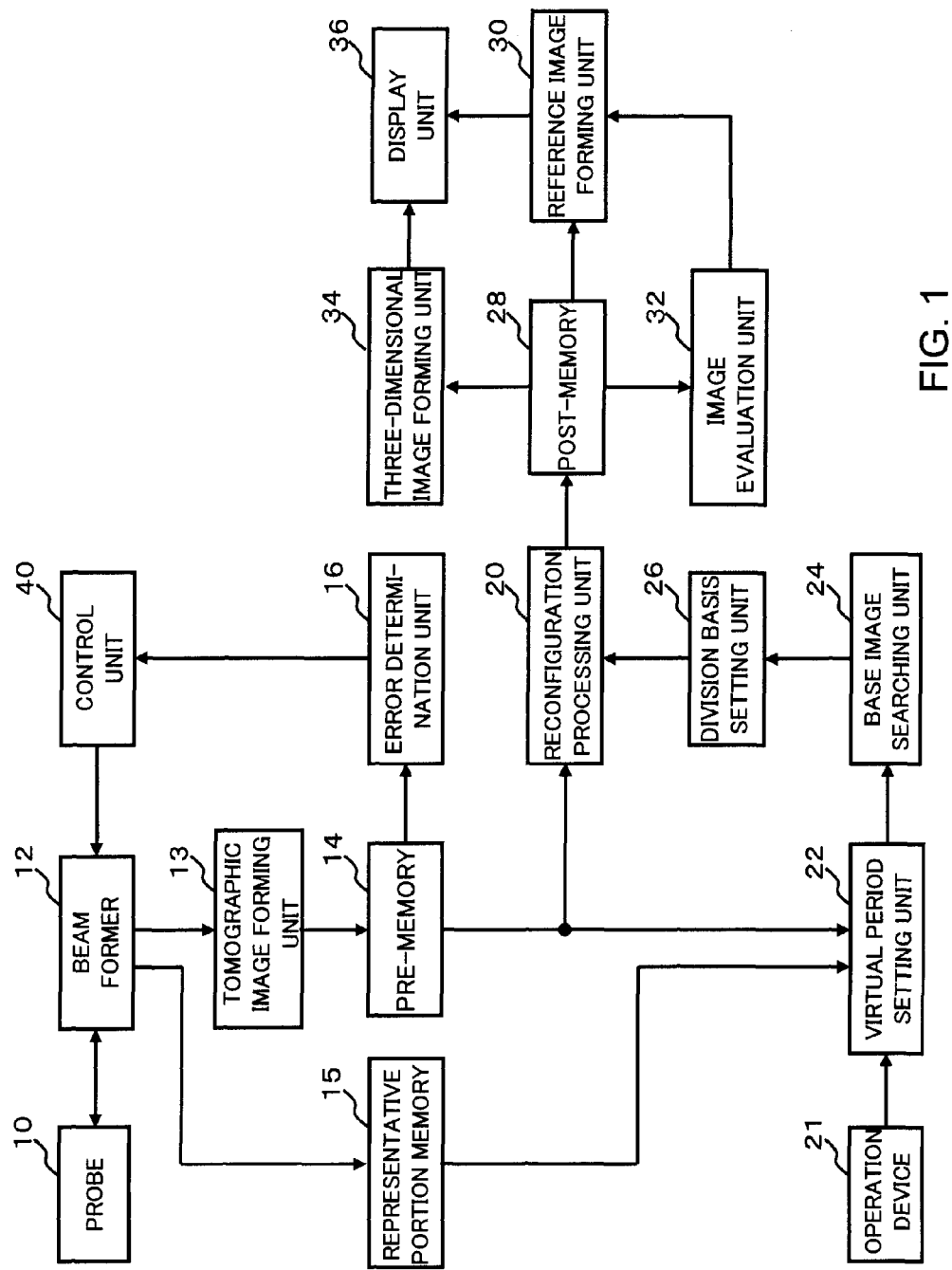
FIG. 1 is a diagram showing the overall structure of an ultrasound diagnostic apparatus which is a preferred embodiment of the present invention.

FIG. 1 is a diagram illustrating the overall configuration of an ultrasound diagnostic apparatus which is a preferred embodiment of the present invention. A probe 10 emits and receives ultrasonic waves within a three-dimensional region including an object. The probe 10 has a plurality of vibration elements that emit and receive ultrasonic waves, and are controlled by a beam former 12 so as to form emission beams. The vibration elements also receive ultrasonic waves reflected from the object, and output signals obtained therefrom to the beam former 12, whereby the beam former 12 forms reception beams.

The probe 10 of the present embodiment is a 3D probe which scans ultrasonic beams (emission beams and reception beams) within the three-dimensional region and acquires echo data in three dimensions. For example, by mechanically moving a scanning plane which is electronically formed by vibration elements arranged in one dimension (1D array vibrators), ultrasonic beams are scanned in three dimensions. Alternatively, it is also acceptable to electronically control vibration elements arranged in two dimensions (2D array vibrators) so as to scan ultrasonic beams in three dimensions.

The beam former 12 forms emission beams of ultrasonic waves by supplying transmission signals corresponding to the respective vibration elements of the probe 10. Further, the beam former 12 forms reception beams of ultrasonic waves by applying a phasing addition process to reception signals obtained from the respective vibration elements of the probe 10, and outputs echo data acquired based on the reception beam.

In the present embodiment, an object is tissue in periodic motion or a fluent material which varies on a periodic basis, such as the heart of a fetus or blood flowing through blood vessels of a fetus. As such, in the below description, a case where an object is the heart of a fetus, which is a preferred example, will be described. In the present embodiment, a scanning plane is displaced over a plurality of periods of motion of the object, which is the heart of a fetus, so that a plurality of scanning planes are formed within a three-dimensional region.

A tomographic image forming unit 13 forms tomographic images corresponding to respective scanning planes based on echo data obtained from the beam former 12. The tomographic image forming unit 13 forms a tissue image similar to a B-mode image, for example, based on the echo intensity (magnitude of the echo) obtained from the echo data.

Figure 2:
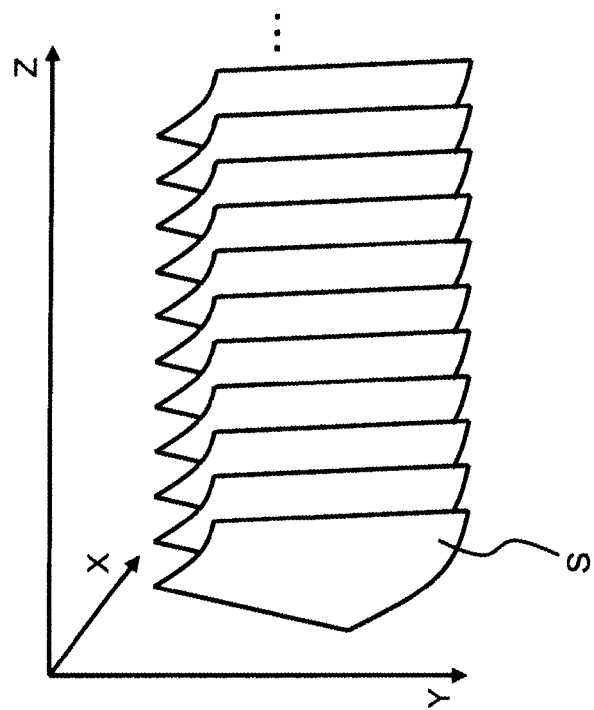
FIG. 2 is an illustration for explaining three-dimensional scanning.

FIG. 2 is an illustration explaining three-dimensional scanning in the present embodiment. In FIG. 2, a three-dimensional region containing an object is expressed in an X-Y-Z Cartesian coordinate system. In the present embodiment, a scanning plane S is formed to be almost parallel to the X-Y plane, and the scanning plane S is gradually displaced in the Z-axis direction such that a plurality of scanning planes S are formed along the Z-axis direction. The scanning plane S is gradually displaced in the Z-axis direction over a plurality of periods of the periodic motion of the heart of the fetus; that is, over a time period in which almost 20 heartbeats are included in about eight seconds, for example.

Turning back to FIG. 1, when a plurality of scanning planes are formed along the Z-axis direction over a plurality of periods of heartbeats of the fetus, the tomographic image forming unit 13 forms tomographic images for the respective scanning planes, and data of the tomographic images corresponding to the scanning planes are sequentially stored in a pre-memory 14.

An error determination unit 16 determines whether a plurality of sets of tomographic image data are favorable, based on the difference amount obtained from the tomographic image data stored in the pre-memory 14. For example, there is a possibility that favorable images cannot be obtained because of large motion of the heart of the fetus within the images due to motion of the fetus, motion of the mother's body, or motion of the probe. As such, the error determination unit 16 determines whether or not images favorable for diagnosis are obtained. When determining, the error determination unit 16 utilizes a cross-sectional difference value which is defined by the following Equation 1:

Cross-sectional difference value $[Z] =$ (1)

$$\sum_{x=0}^{m}\sum_{y=0}^{n}|p(x, y, z) - p(x, y, z+1)|$$

In Equation 1, x, y, and z represent coordinate values along the respective axes in the X-Y-Z Cartesian coordinate system, and p represents a pixel value corresponding to each coordinate within the tomographic image data. From Equation 1, a difference value between two adjacent sets of tomographic image data in the Z-axis direction is calculated.

Figure 3:
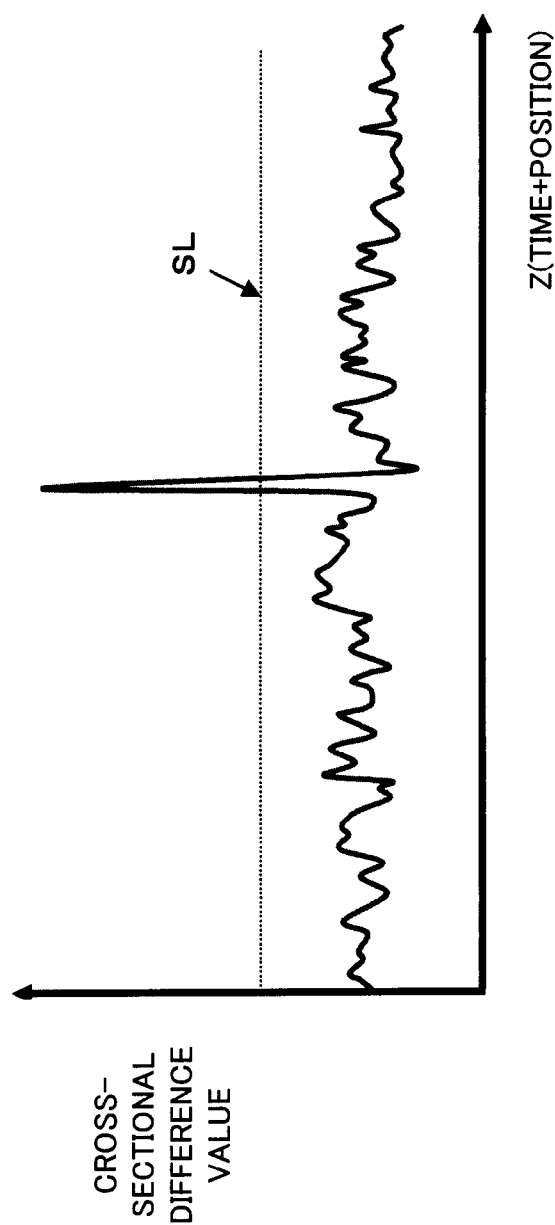
FIG. 3 is a graph showing changes in a cross-sectional difference value.

FIG. 3 is a graph showing changes in the tomographic difference value, in which the horizontal axis in FIG. 3 shows positions of respective sets of tomographic image data. In other words, the horizontal axis in FIG. 3 indicates the positions of the respective scanning planes and the times at which the respective scanning planes are obtained, which corresponds to the Z axis (displacement direction of the position as time elapses) in FIG. 2.

Without large motion of the heart of the fetus, adjacent sets of tomographic image data will be similar to each other, and a difference value obtained from Expression 1 will be relatively small. On the other hand, in the case where the fetus moves, the mother takes a breath, the position of the probe is displaced a long distance, or the like, the heart of the fetus moves a long distance within the tomographic images, so that a difference value between the adjacent sets of tomographic image data will be relatively large. As such, the error determination unit 16 determines that the object, such as a heart, moves a long distance if a tomographic difference value exceeds a predetermined threshold (SL).

Turning back to FIG. 1, when the error determination unit 16 determines that the object is displaced a long distance, a control unit 40 controls, for example, the beam former 12 to stop acquisition of the tomographic image data. It should be noted that the control unit 40 controls each unit shown in FIG. 1, and when the error determination unit 16 determines that there is an error, for example, the control unit 40 may allow a display unit 36 to display the error or alert the operator of error. When the error determination unit 16 does not determine that there is an error, the processes described below will be carried out based on a plurality of sets of tomographic image data stored in the pre-memory 14.

A virtual period setting unit 22 calculates a virtual period, which serves as a temporary period relating to the heart of the fetus, based on the tomographic image data stored in the pre-memory 14. When calculating the virtual period, the virtual period setting unit 22 uses a mutual difference value defined from the following Equation 2.

Mutual Difference Value $[z] =$ (2)

$$\sum_{w=0}^{l}\sum_{x=0}^{m}\sum_{y=0}^{n}|p(x, y, z+w) \times \{p(x, y, z+w) - p(x, y, z+w+1)\}|$$

In Equation 2, x, y, and z represent coordinate values along the respective axes in the X-Y-Z Cartesian coordinate system, and p represents a pixel value corresponding to each coordinate within the tomographic image data. In Equation 2, a difference between two pixel values of two adjacent sets of tomographic image data in the Z-axis direction is multiplied by one of the pixel values. Thereby, the mutual difference value becomes larger when the heart dilates, as compared with the case where the heart contracts. As such, dilation and contraction, which are less likely to be distinguished by a simple difference value, can be distinguished by the mutual difference value.

For example, in tomographic image data set z, it is assumed that a pixel p(x, y, z) represents a cardiac muscle near the inner wall of the heart, and that the pixel value of p(x, y, z)=100. When the heart dilates and the cardiac cavity becomes larger, in tomographic image data set z+1 which is obtained following the tomographic image data set z, a pixel p(x, y, z+1) represents the cardiac cavity. As the pixel value of the cardiac cavity is smaller than that of the cardiac muscle, it is assumed that the pixel value of p(x, y, z+1)=10. In this example, the absolute value of the right side of Equation 2 is 100*(100−10)=9000. When the heart dilates, as pixels representing the cardiac muscle are changed to those representing the cardiac cavity in large proportion near the inner wall of the heart, the mutual difference value calculated from Equation 2 becomes relatively large.

On the contrary, when the heart contracts, a phenomenon opposite that of the above example will be caused. This means that as the cardiac cavity becomes smaller when the heart contracts, a pixel p(x, y, z)=10 corresponding to the cardiac cavity is changed to a pixel p(x, y, z+1)=100 corresponding to the cardiac muscle. In this example, the absolute value of the right side of Equation 2 is |10*(10−100)|=900, which is smaller than the value 9000 of the case of dilation. As such, dilation and contraction can be distinguished by the mutual difference value.

Figure 4:
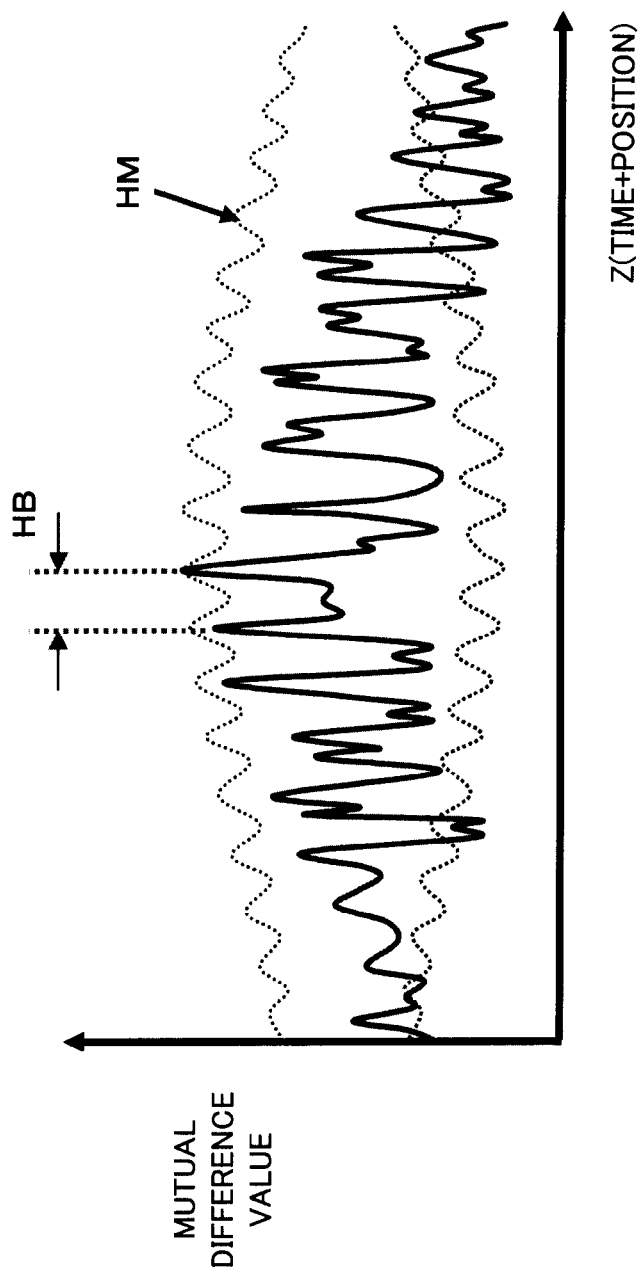
FIG. 4 is a graph showing changes in a mutual difference value.

FIG. 4 is a graph showing changes in the mutual difference value. In FIG. 4, the horizontal axis indicates positions of the respective sets of tomographic image data (positions and times of respective scanning planes), and corresponds to the Z axis (displacement direction of the position as time elapses) in FIG. 2. When mutual difference values are calculated at respective positions (z) on the Z axis from Equation 2, the mutual difference values become relatively large when the heart dilates. As such, the virtual period setting unit 22 detects peak values (local maximum values) of the mutual difference values, and determines an interval (HB) between adjacent peak values to be a period of the heart (period of a heartbeat). FIG. 4 also shows a waveform corresponding to the motion (HM) of the inner wall of the heart of the fetus.

For example, there is a case where the heartbeat period may vary in the heart of a fetus. When the heartbeat period varies, intervals between peak values also vary. As such, the virtual period setting unit 22 sets a second largest interval among the intervals of peak values as a virtual period, for example. It should be noted that a value of largest frequency or a center-of-gravity value, which can be obtained from histogram of intervals between peak values, may be set as a virtual period.

Further, a user or the apparatus may select a virtual period among a plurality of preset values, or a user may input a value of a virtual period by means of an operation device 21, for example. Alternatively, a fixed value may always be used as a virtual period.

Turning back to FIG. 1, in addition to the acquisition of three-dimensional echo data (reception signals) described above, in the present embodiment, echo data are acquired from a representative portion of the object over a plurality of periods relating to the motion of the object. For example, a scanning plane is fixedly formed near the center of the heart of the fetus which is the object, and a plurality of sets of echo data (reception signals) of a plurality of time phases are acquired from the scanning plane over a time period (e.g., 1 to 2 seconds) including a plurality of heartbeats. The sets of echo data acquired from the representative portions are stored in a representative portion memory 15. For example, following the acquisition of the three-dimensional echo data to be stored in the pre-memory 14, echo data from the representative portion to be stored in the representative portion memory 15 will be acquired. Of course, echo data to be stored in the pre-memory 14 may be acquired after the acquisition of the echo data to be stored in the representative portion memory 15.

The virtual period setting unit 22 may calculate a virtual period based on the echo data of a plurality of time phases stored in the representative portion memory 15. Even in this case, the virtual period setting unit 22 uses the mutual difference values defined by the above-described Equation 2.

It should be noted that when using echo data of a plurality of time phases stored in the representative portion memory 15, x and y in Equation 2 represent coordinate values along the respective axes of the X-Y Cartesian coordinate system of FIG. 2, and p represents a pixel value corresponding to each coordinate within the scanning plane (within the tomographic image) fixedly set in the representative portion. Further, z in Equation 2 represents time. This means that in Equation 2, a difference between two pixel values, of two sets of tomographic image data corresponding to two adjacent points of time, is multiplied by one of the pixel values. Thereby, the mutual difference value becomes relatively larger when the heart dilates as compared with the case where the heart contracts, so that dilation and contraction of the heart, which is difficult to distinguish with a simple difference value, can be distinguished. As such, changes in the mutual difference value which are similar to those in FIG. 4 can be acquired.

Even in the case of using echo data of a plurality of time phases stored in the representative portion memory 15, the virtual period setting unit 22 sets a representative (e.g., second largest) interval, among intervals between peak values in the changes in the mutual difference value, as a virtual period. It should be noted that an average value of the intervals between the peak values, or a largest frequency value or a center-of-gravity value obtained from histograms of the intervals of the peak values, may be set as a virtual period.

Further, when setting a virtual period, M-mode measurement may be used. For example, if the object is the heart of a fetus, an ultrasonic beam is fixedly set near the center of the heart of the fetus, and from the ultrasonic beam, echo data (beam data) of a plurality of time phases are acquired over the time period including a plurality of heartbeats. Even in this case, the acquired echo data are stored in the representative portion memory 15. In the case of beam data, x in Equation 2 becomes a fixed value according to the position of the ultrasonic beam. By calculating mutual difference values based on Equation 2 over the plurality of points of time (z), a periodic waveform similar to that of FIG. 4 is formed even in the case of beam data, and a representative interval among the intervals of the peak values or an average value of the intervals of the peak values is set as a virtual period, as in the case of tomographic image data.

When the virtual period is set, a base image searching unit 24 searches for a plurality of base images from the plurality of sets of tomographic image data using the virtual period. This searching is performed using the mutual difference values obtained by applying Equation 2 to the plurality of sets of tomographic image data stored in the pre-memory 14.

Figure 5A:
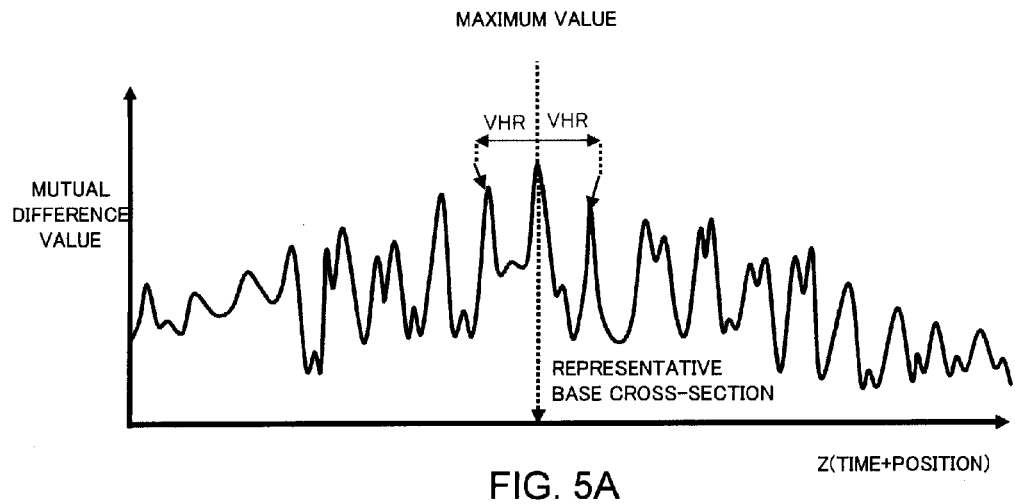
FIG. 5 shows graphs for explaining searches for base images.
Figure 5B:
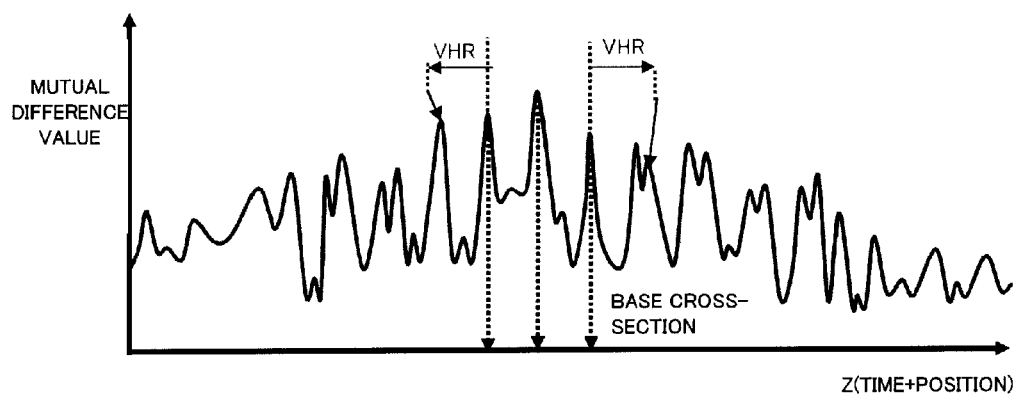
Figure 5C:
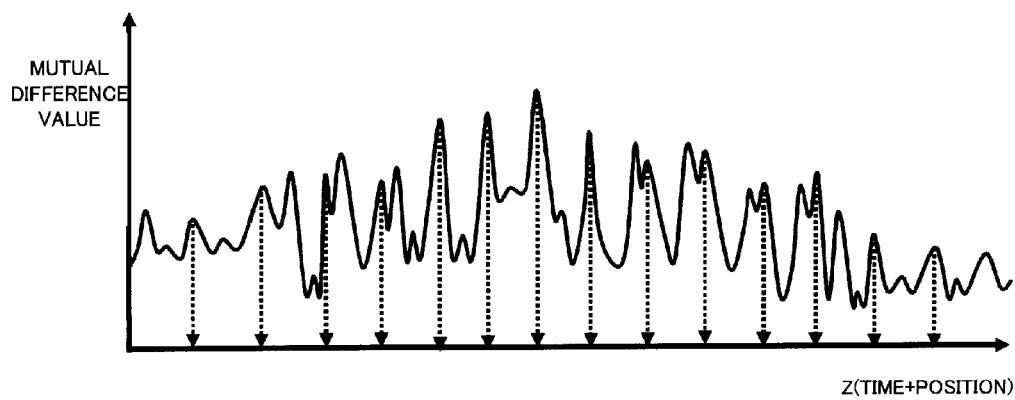

FIG. 5 shows graphs for explaining searching of base images. FIGS. 5(A) to 5(C) respectively show changes in the mutual difference values which have been described by reference to of FIG. 4. The base image searching unit 24 first searches for a base image serving as a representative (representative base image) from a plurality of tomographic images. As shown in FIG. 5(A), the base image searching unit 24 sets tomographic image data corresponding to the position where the mutual difference value becomes a maximum, as a representative base image (representative base cross-section). Then, the base image searching unit 24 uses the representative base image as a starting point to sequentially search for tomographic images, which are closest to the positions distant by the virtual period, from a plurality of tomographic images corresponding to the local maximum mutual difference values.

First, as shown in FIG. 5(A), the base image searching unit 24 searches for tomographic images which are closest to the positions distant from the representative base image by the virtual period (VHR) in the positive direction and the negative direction in the Z axis direction, and sets them as base images. Then, as shown in FIG. 5(B), the base image searching unit 24 searches for tomographic images which are closest to the positions distant from the searched base images by the virtual period (VHR) and sets them as new base images. In FIG. 5(B), arrows of dotted lines show positions of a plurality of base images (base cross-sections).

The base image searching unit 24 uses the representative base image as a starting point and sequentially searches for a plurality of base images. In this way, a plurality of base images are searched from a plurality of tomographic images corresponding to the local maximum mutual difference values, as shown in FIG. 5(C). In FIG. 5(C), arrows of dotted lines show the positions of a plurality of base images (base cross-sections).

Turning back to FIG. 1, when the base images have been searched, a division basis setting unit 26 sets a plurality of division bases according to the base images within an image string configured of a plurality of tomographic images (data). The division basis setting unit 26 may set the respective base images as division bases, for example.

When a plurality of division bases are set, a reconfiguration processing unit 20 divides the image string into a plurality of image groups, with the respective division bases serving as the boundaries for the division. Then, the reconfiguration processing unit 20 extracts, from the respective image groups, a plurality of tomographic images which correspond to one another on a periodic basis to thereby realize the reconfiguration process (reconstruction process). The reconfiguration processing unit 20 reconfigures the tomographic image data stored in the pre-memory 14 and stores them in a post-memory 28.

Figure 6:
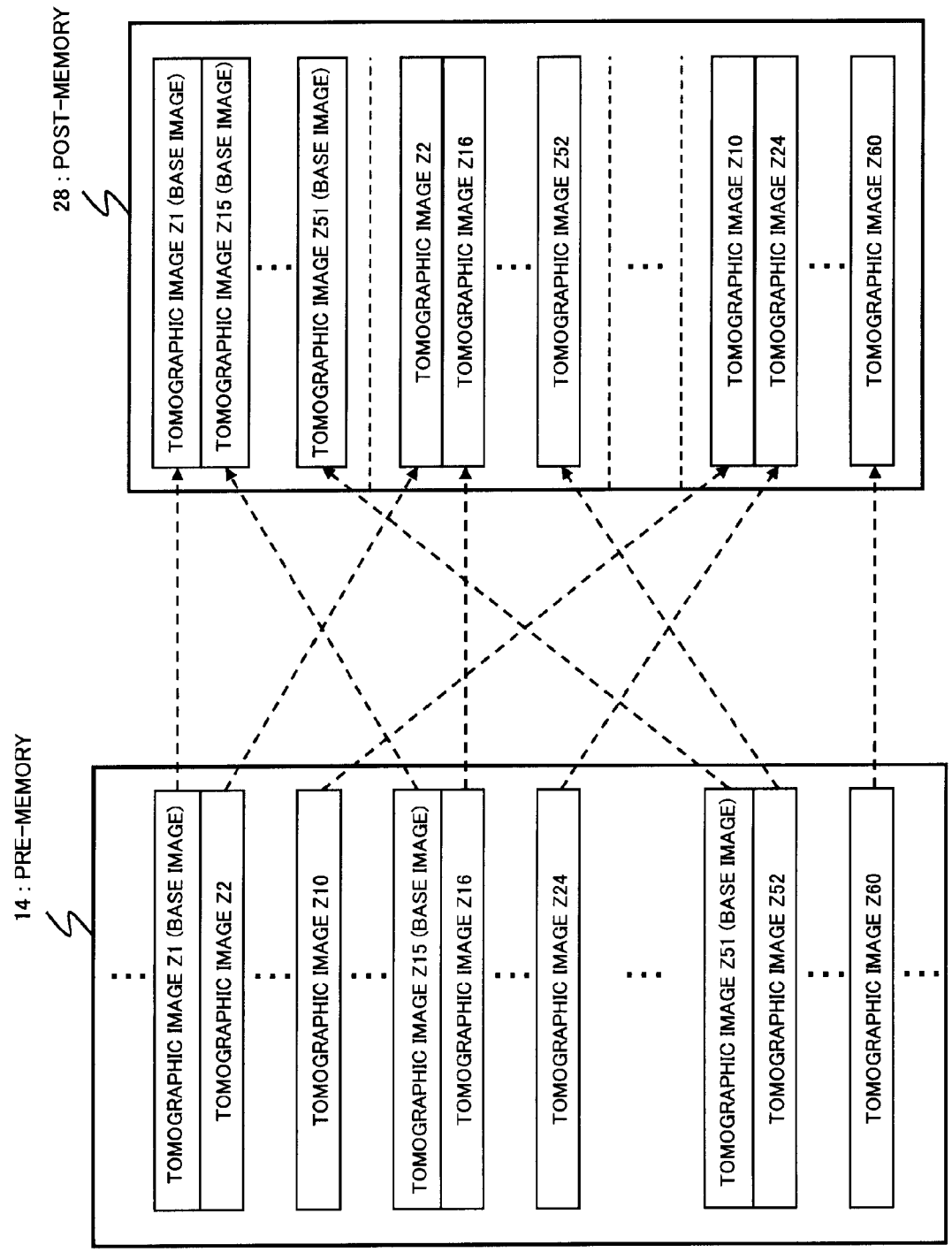
FIG. 6 is a diagram for explaining a set of processes performed by a reconfiguration processing unit 20.

FIG. 6 is a diagram for explaining a process performed by the reconfiguration processing unit 20. FIG. 6 shows a correspondence relationship between data to be stored in the pre-memory 14 and data to be stored in the post-memory 28. In FIG. 6, "tomographic image Zn (n=1, 2, 3, . . . , 60)" represents tomographic image data at a position of a coordinate Zn along the Z axis (see FIG. 2).

In the pre-memory 14, a plurality of sets of tomographic image data corresponding to a plurality of scanning planes sequentially formed along the Z-axis direction are stored in the order of formation. This means that in the pre-memory 14, following some tomographic images, a plurality of tomographic image data are stored in the order of a tomographic image Z1, a tomographic image Z2, . . . a tomographic image Z60, . . . .

The reconfiguration processing unit 20 sets the respective base images as the division boundaries to divide the tomographic images (data) stored in the pre-memory 14 into a plurality of image groups. Then, a plurality of tomographic images which correspond to one another on a periodic basis are extracted from the image groups.

In FIG. 6, the tomographic image Z1, a tomographic image Z15, . . . , and a tomographic image Z51 are a plurality of base images searched by the base image searching unit 24. The reconfiguration processing unit 20 first extracts the tomographic image Z1, the tomographic image Z15, . . . and the tomographic image Z51, which are bases images, as a plurality of sets of tomographic image data corresponding to one another on a periodic basis. Then, the extracted tomographic image Z1, tomographic image Z15, . . . and tomographic image Z51 are stored in the post-memory 28 as one data block.

Next, the reconfiguration processing unit 20 extracts a plurality of tomographic images, which are adjacent to the respective base images in the positive direction of the Z axis, as a plurality of sets of tomographic image data which correspond to one another on a periodic basis. As such, a tomographic image Z2, a tomographic image Z16, . . . and a tomographic image Z52 are extracted and stored in the post-memory 28 as one data block.

Further, the reconfiguration processing unit 20 extracts a plurality of tomographic images which are adjacent to the tomographic image Z2, the tomographic image Z16, . . . and the tomographic image Z52, respectively, in the positive direction of Z axis. In this way, with use of the respective base images as starting points, data blocks of a plurality of tomographic images corresponding to one another on a periodic basis are sequentially extracted and stored in the post-memory 28.

It should be noted that according to the above-described reconfiguration process, some tomographic images among the tomographic images stored in the pre-memory 14 are not used for the reconfiguration process. For example, tomographic images (Z11 to Z14) between the tomographic image Z10 and the tomographic image Z15 in the pre-memory 14 are not used for the reconfiguration process.

Further, in the above-described reconfiguration process, a plurality of data blocks are formed in the post-memory 28 after the reconfiguration process. For example, the tomographic image Z1, the tomographic image Z15, . . . and the tomographic image Z51 constitute one data block, and the tomographic image Z2, the tomographic image Z16, . . . and the tomographic image Z52 constitute the next data block. The number of data blocks formed in the post-memory 28 through the reconfiguration process corresponds to the number of tomographic images in an image group containing the smallest number of tomographic images, among a plurality of image groups formed by division according to the base images. For example, if a plurality of base images are searched as shown in FIG. 5(C), the number of tomographic images in an image group corresponding to a section having a shortest interval between two adjacent base images and the number of data blocks in the post-memory 28 shown in FIG. 6 conform with each other.

As such, after a plurality of base images are searched as shown in FIG. 5(C), by checking the number "e" of the tomographic images in an image group corresponding to a section having the shortest interval between two adjacent base images, setting the number as the number "e" of the data blocks, and ending the reconfiguration process when the number of the data blocks reaches "e" as a result of the reconfiguration process, for example, it is possible to reduce (desirably, to completely eliminate) unnecessary steps in the reconfiguration process.

Further, if the division basis setting unit 26 sets a plurality of division bases at positions distant from respective base images by a specified interval, a plurality of data blocks can be formed around a data block corresponding to the base image.

Figure 7:
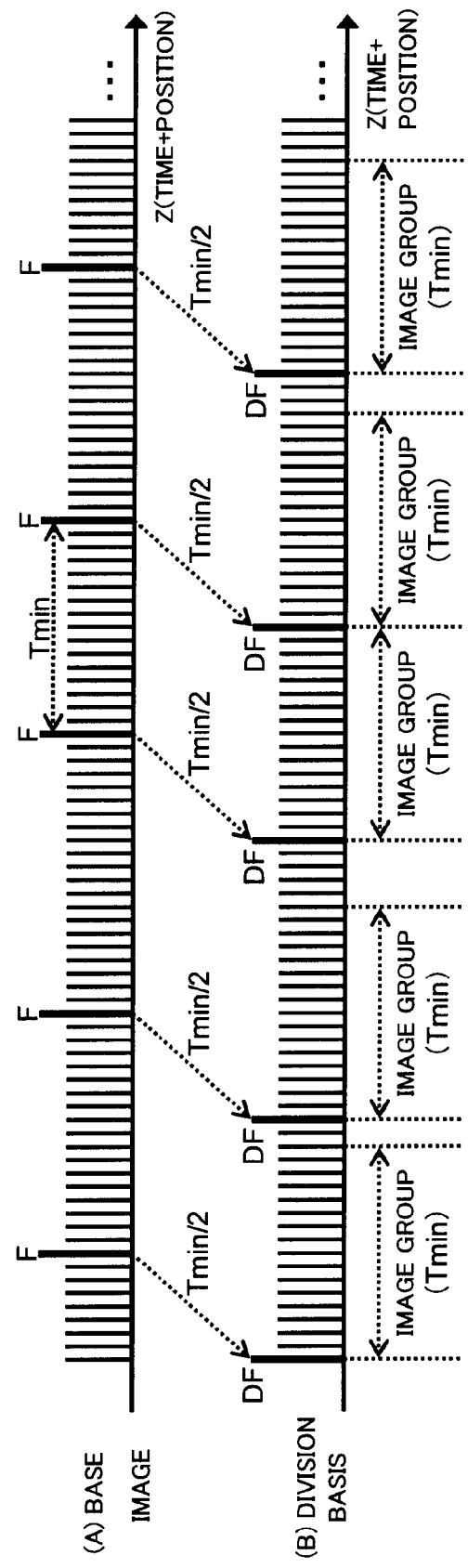
FIG. 7 is an illustration for explaining setting of division bases distant by a specified interval.

FIG. 7 is an illustration for explaining settings of division bases which are distant by a specified interval. Each of FIGS. 7(A) and 7(B) shows an image string constituted of a plurality of tomographic images stored in the pre-memory 14. This means that in each of the drawings, a horizontal axis shows a position of tomographic images (position and time of scanning plane), and a plurality of tomographic images are shown by solid lines in pulses along the horizontal axis.

In FIG. 7(A), a plurality of base images F, searched within the image string, are shown by bold, long, solid lines. The base images F are searched according to a virtual period and changes in the mutual difference value (see FIG. 5). As such, an interval between adjacent base images F varies according to the periodic changes in motion of the object.

Accordingly, the division basis setting unit 26 sets a specified interval based on intervals between a plurality of base images F. For example, a specified interval may be set based on a minimum interval among the intervals between respective adjacent base images F. In FIG. 7(A), the minimum interval is a time period Tmin, and the division basis setting unit 26 sets the specified interval as Tmin/2, which is half of the minimum time period.

Then, the division basis setting unit 26 sets a plurality of division bases DF at positions going back in terms of time by a specified interval from the respective base images F within the image string. FIG. 7(B) shows a plurality of division bases DF, set within the image string which is the same as that of FIG. 7(A), as bold, long, solid lines.

In this way, when the division bases DF are set within the image string, the image string is divided into a plurality of image groups, with the respective division bases DF serving as the boundaries for the division. In FIG. 7(B), one image group is constituted of a plurality of tomographic images included in a time period Tmin starting from each division basis DF. Then, by extracting a plurality of tomographic images which correspond to one another on a periodic basis from the respective image groups as described below, reconfiguration (reconstruction) of images is realized.

It should be noted that in the above-described reconfiguration process performed through division, only tomographic images belonging to the image groups within the time periods Tmin shown in FIG. 7(B) are used for the reconfiguration process. As such, tomographic images which are present between two adjacent image groups are not used for the reconfiguration process.

Figure 8:
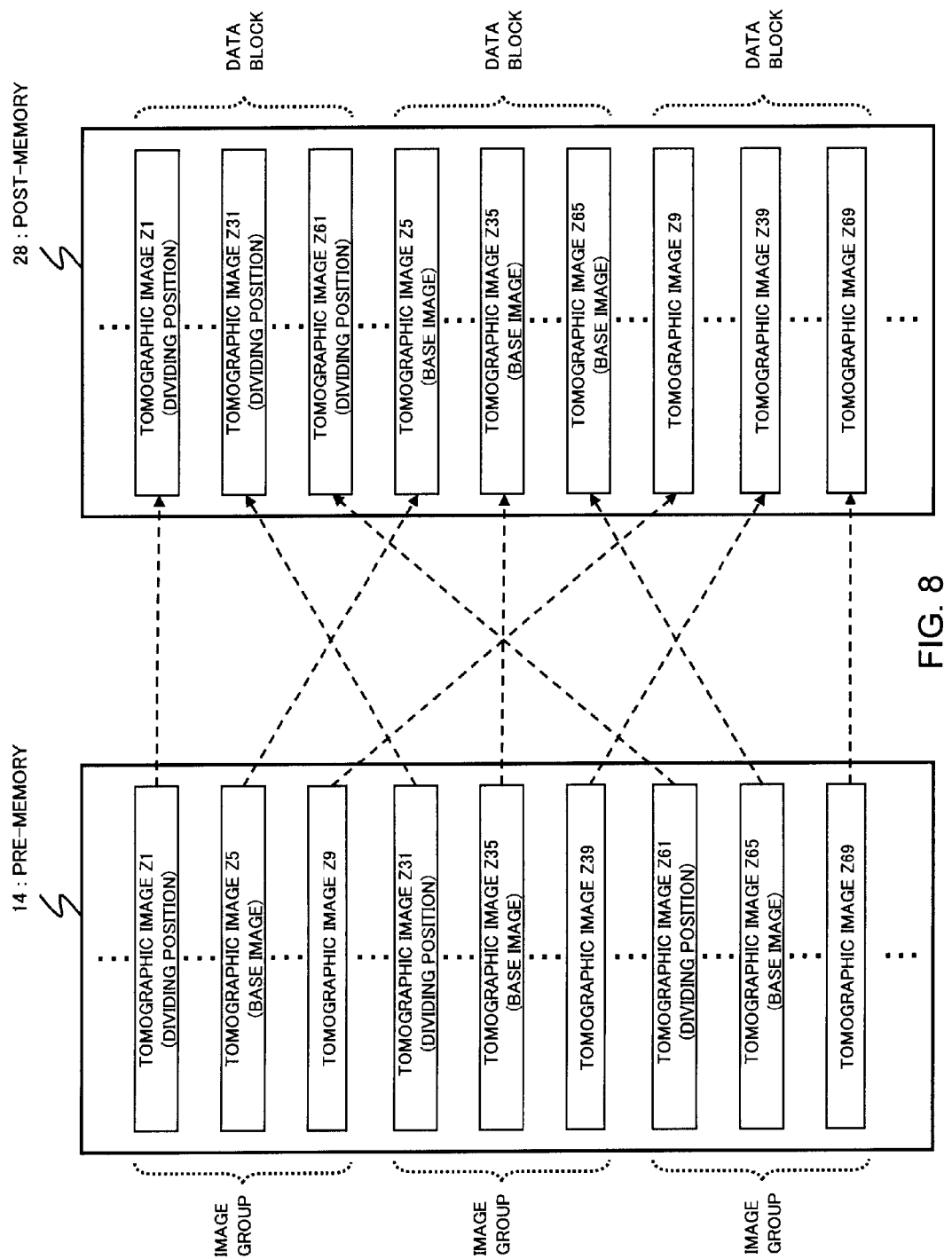
FIG. 8 is a diagram for explaining another set of processes performed by the reconfiguration processing unit 20.

FIG. 8 is a diagram for explaining another set of processes performed by the reconfiguration processing unit 20. Similar to FIG. 6, FIG. 8 shows a correspondence relationship between data to be stored in the pre-memory 14 and data to be stored in the post-memory 28.

In the example shown in FIG. 8, the reconfiguration processing unit 20 divides the tomographic images (data) stored in the pre-memory 14 into a plurality of image groups with use of the division bases as respective boundaries for the division. Then, a plurality of tomographic images which correspond to one another on a periodic basis are extracted from the respective image groups.

In FIG. 8, a tomographic image Z5, a tomographic image Z35, and a tomographic image Z65 are base images searched by the base image searching unit 24, and a tomographic image Z1, a tomographic image Z31, and a tomographic image Z61 are division bases set by the division basis setting unit 26.

The reconfiguration processing unit 20 first extracts the tomographic image Z1, ..., the tomographic image Z31, ..., and the tomographic image Z61, which are the division bases, as tomographic images which correspond to one another on a periodic basis, and stores them in the post-memory 28 as one data block.

Next, the reconfiguration processing unit 20 extracts a plurality of tomographic images which are adjacent to the respective division bases in the Z-axis direction as a plurality of tomographic images which correspond to one another on a periodic basis, and stores the extracted tomographic images in the post-memory 28 as one data block. Further, the reconfiguration processing unit 20 sequentially forms data blocks constituted of a plurality of tomographic images which correspond to one another on a periodic basis, and stores them in the post-memory 28.

In the process of sequentially forming a plurality of data blocks, the tomographic image Z5, ..., the tomographic image Z35, ..., and the tomographic image Z65, which are base images, are stored in the post-memory 28 as one data block, and a tomographic image Z9, ..., a tomographic image Z39, ..., and a tomographic image Z69, which are the last images in the respective image groups, are stored the post-memory 28 as one data block, whereby formation of data blocks has been completed. This means that the reconfiguration process has been completed. In this reconfiguration process, some tomographic images, among the entire tomographic images, are not used in the reconfiguration process, as was described with reference to FIG. 7.

According to the reconfiguration process described with reference to FIG. 8, a set of three-dimensional image data of a heading time phase is formed based on the tomographic image Z1, ..., the tomographic image Z31, ..., and the tomographic image Z61 stored in the post-memory 28, and another set of three-dimensional image data of a central time phase is formed based on the tomographic image Z5, ..., the tomographic image Z35, ..., and the tomographic image Z65. As such, it is possible to arrange three-dimensional image data constituted of base images, which may have the most closely conforming time-phase relationship with one another, at the center of the time phases. Further, as the base images are images of time phases corresponding to a late stage of dilation of the heart, for example, a time phase corresponding to the late stage of dilation can be arranged at the center of the time phases so as to be observed without fail.

It should be noted that by appropriately changing the specified interval described with reference to FIG. 7, a data block corresponding to the base images can be shifted from the center of all the data blocks. As such, a user may appropriately set a specified interval (e.g., time and the number of frames) so as to allow a data block corresponding to base images to shift from the center.

Turning back to FIG. 1, a reference image forming unit 30 forms a reference image indicating temporal changes in the form of the object caused by the motion, based on the image string after the reconfiguration process stored in the post-memory 28. The reference image forming unit 30 forms a tomographic image of the object by a plane orthogonal to the scanning plane, and also displays a dilated portion and a contracted portion of the object in different display modes, within the tomographic image.

Figure 9:
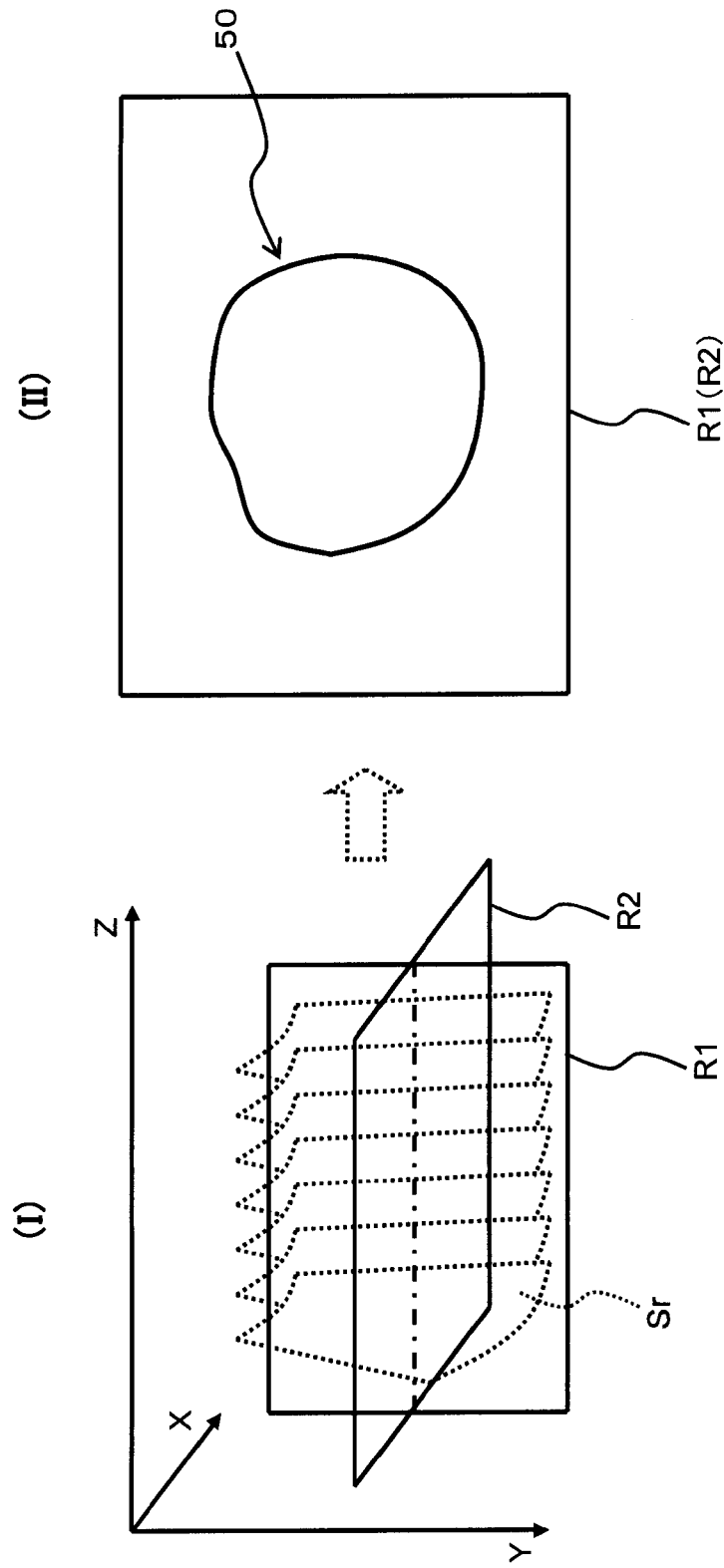
FIG. 9 is an illustration for explaining a tomographic image of an object formed as a reference image.

FIG. 9 is an illustration for explaining a tomographic image of the object formed as a reference image. FIG. 9(I) shows a plurality of tomographic images Sr included in the image string after the reconfiguration process. The X-Y-Z coordinate system in FIG. 9(I) corresponds to the X-Y-Z coordinate system before the reconfiguration process in FIG. 2. From the tomographic images corresponding to the scanning planes S in FIG. 2, a plurality of tomographic images Sr in FIG. 9, which correspond to one another on a periodic basis, are extracted through the reconfiguration process. These tomographic images Sr may be the tomographic image Z1, the tomographic image Z15, ..., and the tomographic image Z51 stored in the post-memory 28 shown in FIG. 6, for example, and these tomographic images Sr constitute a reconfigured image of a time phase (e.g., phase T1).

The reference image forming unit 30 sets a plane R1 or a plane R2 with respect to the reconfigured image constituted of the tomographic images Sr. The plane R1 is parallel to the Y-Z plane and orthogonal to the tomographic images Sr (scanning plane). The plane R2 is parallel to the Z-X plane and orthogonal to the tomographic images Sr (scanning plane). It is desirable to set the plane R1 and the plane R2 to include the center portion of the object. For example, a user may designate the position of the plane R1 or the plane R2 within the display image while viewing the display image after the reconfiguration. Alternatively, the reference image forming unit 30 may identify the object portion within the reconfigured image by means of a binarization process or the like and set the plane R1 or the plane R2 so as to run through the center of gravity of the object portion.

When the plane R1 or the plane R2 is set, the reference image forming unit 30 forms a tomographic image 50 by means of the plane R1 or the plane R2, as shown in FIG. 9 (II). The reference image forming unit 30 also displays the dilated portion and the contracted portion of the object in different display modes within the tomographic image 50.

Figure 10:
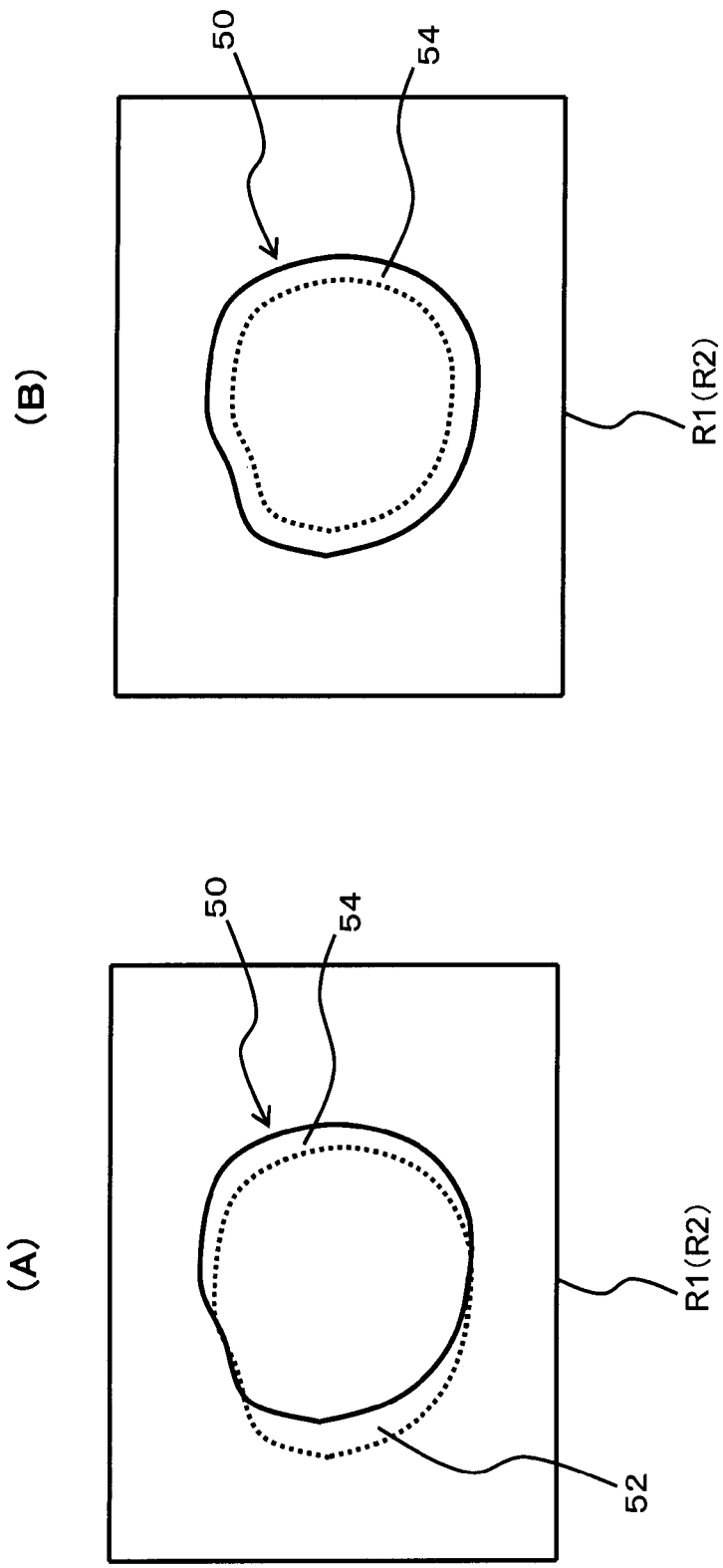
FIG. 10 is an illustration for explaining display modes of the object in reference images.

FIG. 10 is an illustration for explaining the display modes of the object within the reference image. The reference image forming unit 30 displays the dilated portion and the contracted portion of the object in different display modes within the tomographic image 50 of the object. The reference image forming unit 30 forms tomographic images 50 of the object by means of the plane R1 (or the plane R2) over a plurality of time phases. Then, for each of the time phases, the reference image forming unit 30 extracts the object by means of a binarization process or the like, and distinguishes the object from the other tissue. For example, if the object is a heart, as echo values are smaller inside the heart (cardiac cavity) compared with other tissues, portions of smaller echo values are extracted through a binarization process or the like to thereby distinguish the inside of the heart (cardiac cavity) from the other tissue. Of course, a well-known process such as a noise reduction process or a labeling process may be used in addition to the binarization process so as to improve the accuracy of the extraction.

When the tomographic images 50 of the object are extracted over the respective time phases, the reference image forming unit 30 identifies a dilated portion and a contracted portion from the changes in the tomographic images 50 between time phases. For example, if an image portion corresponding to another tissue at a time phase T1 changes to an image portion corresponding to the object at the next time phase T2, the image portion is determined to be a dilated portion. On the other hand, if an image portion corresponding to the object at the time phase T1 changes to an image portion corresponding to another type of tissue at the next time phase T2, the image portion is determined to be a contracted portion.

FIGS. 10(A) and 10(B) show examples of displayed forms. The reference image forming unit 30 displays the dilated portion of the tomographic image 50 in a cold color such as blue or green, and displays the contracted portion in a warm color such as red or yellow, for example.

For example, as shown in FIG. 10(A), when the tomographic image 50 has changed from a state of one time phase ago indicated by a dotted line to a state indicated by a solid line, an area 54 surrounded by the dotted line and the solid line is determined to be the dilated portion, and is expressed in a cold color. Further, an area 52 surrounded by the dotted line and the solid line is determined to be a contracted portion, and is expressed in a warm color. The state shown in FIG. 10(A) includes the area 54 corresponding to the dilated portion and the area 52 corresponding to the contracted portion, and this state corresponds to a distorted moving image in which the object (e.g., heart) is dilated partially and contracted partially.

In contrast, in the state shown in FIG. 10(B), the area 54 surrounded by the dotted line and the solid line is determined to be a dilated portion, and the object (e.g., heart) is dilated uniformly as a whole. This corresponds to a less distorted (desirably, completely undistorted) moving image.

It should be noted that the dilated portion may be expressed in a warm color and the contracted portion may be expressed in a cold color, or may be in another color. Further, different filling patterns or the like may be used rather than colors.

Turning back to FIG. 1, when the reference image is formed by the reference image forming unit 30, the reference image is displayed on the display unit 36. A user (examiner) of the ultrasound diagnostic apparatus of FIG. 1 looks at the reference image displayed on the display unit 36 and evaluates distortion in the moving image of the object such as a heart. If the distortion is large (e.g., the image of FIG. 10(A)), the user modifies the virtual period by means of the operation device 21.

The virtual period setting unit 22 modifies the virtual period according to an instruction from the user. Then, based on the modified virtual period, the base image searching unit 24 searches for a plurality of base images, and based on these base images, the division basis setting unit 26 sets a plurality of division bases, and the reconfiguration processing unit 20 carries out a reconfiguration process. According to the reconfigured image string obtained in this manner, the reference image forming unit 30 forms a reference image, and the user looks at the reference image to evaluate the distortion. Modification of the virtual period and evaluation of the distortion are repeated so as to adjust the virtual period to reduce the distortion.

An image evaluation unit 32 calculates an evaluation value serving as an index to be used by the user when evaluating the distortion. The image evaluation unit 32 extracts a plurality of images corresponding to the same position of the object from the image string of different time phases stored in the post-memory 28, and calculates a difference value between the extracted images. The image evaluation unit 32 calculates, as a difference value, an inter-volume difference value from the following Equation 3.

$$\text{Inter-volume difference value} = \sum_{x=0}^{m}\sum_{y=0}^{n}\left|p\left(x, y, \frac{Z}{2}, v\right) - p\left(x, y, \frac{Z}{2}, v-1\right)\right| \quad (3)$$

In Equation 3, x, y, and z represent coordinate values along the respective axes in the X-Y-Z Cartesian coordinate system in FIG. 9(I), and p represents a pixel value corresponding to each coordinate within the tomographic image data. Further, v represents a volume number (time phase), and a coordinate Z/2 represents a center position in the Z-axis direction; that is, the center position of the object, for example. From Equation 3, a difference value between two sets of tomographic image data at the center position in the Z-axis direction is calculated, which is obtained from the reconfigured images of a volume v and a volume (v−1).

The difference value calculated by the image evaluation unit 32 is displayed on the display unit 36 together with the reference image formed by the reference image forming unit 30, for example. For example, adjacent to the tomographic image 50 displayed as shown in FIG. 10(A) or 10(B), a bar of length corresponding to the magnitude of the difference value is displayed. As a matter of course, the magnitude of the difference value may be displayed by means of a numerical value.

When the virtual period is modified according to the instruction from the user, and a virtual period for reducing the distortion is set, a three-dimensional image forming unit 34 forms three-dimensional image data projecting the object such as the heart of a fetus three-dimensionally based on the plurality of sets of tomographic image data after the reconfiguration (image string after the reconfiguration) stored in the post-memory 28.

The three-dimensional image forming unit 34 forms three-dimensional image data of each of the time phases based on one data block stored in the post-memory 28. For example, the three-dimensional image forming unit 34 forms three-dimensional image data of each of the time phases based on one data block stored in the post-memory 28 shown in FIG. 8.

The three-dimensional image forming unit 34 forms the three-dimensional image data over respective time phases by applying various methods such as a volume rendering method, an integration method, or a projection method. An image corresponding to the three-dimensional image data formed over the respective time phases in this manner is displayed on the display unit 36, and a three-dimensional moving image is displayed in a pseudo manner in a real time basis. For example, images corresponding to three-dimensional image data of a plurality of time phases may be displayed repeatedly to thereby perform loop reproduction.

According to the above embodiment, even in the case where an object of diagnosis is the heart of a fetus in which periods of heartbeats are unstable, for example, appropriate base images are searched according to variations of the periods so that data blocks are reconfigured. As such, as disturbances in the image caused by variations of the periods are reduced (desirable, completely removed), a highly reliable display image can be acquired.

Further, in the above embodiment, in the case of setting a virtual period using echo data acquired from a representative portion of the object; that is, from a fixed position of the object, the accuracy of setting the virtual period is improved as compared with the case of setting the virtual period from echo data acquired in a moving manner.

Figure 11:
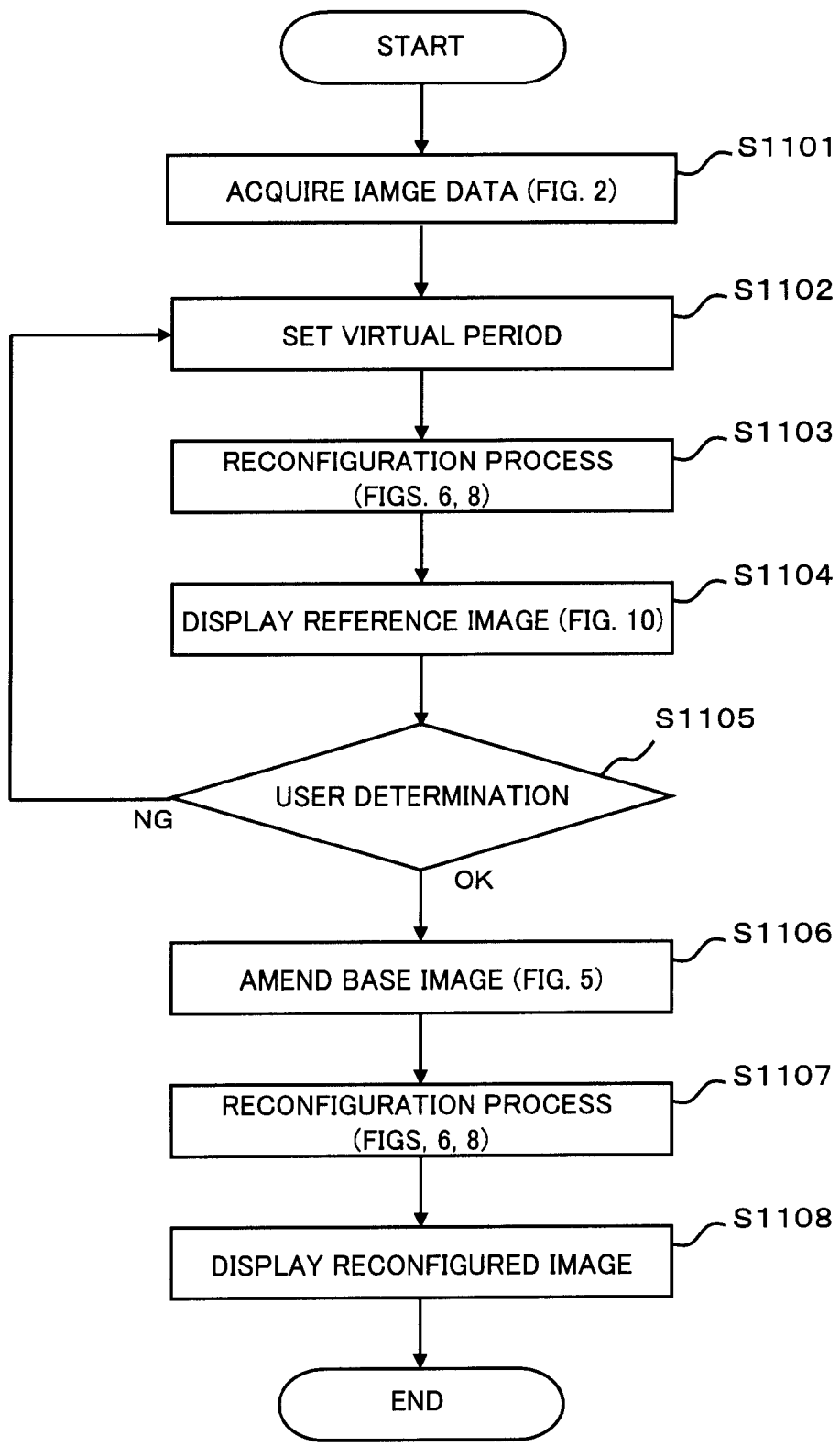
FIG. 11 is a flowchart for explaining a reconfiguration process to reduce distortion.

FIG. 11 is a flowchart for explaining the reconfiguration process in which the distortion is reduced. Processes at respective steps shown in FIG. 11 will be described using the same reference numerals as those in FIG. 1 for the parts (components) shown in FIG. 1.

First, as described with reference to FIG. 2, a plurality of scanning planes are formed along the Z-axis direction over a plurality of periods relating to the motion of the object, and a set of tomographic image data is acquired for each of the scanning planes and stored in the pre-memory 14 (S1101). It should be noted that the error determination unit 16 may determine whether a plurality of sets of tomographic image data are favorable, based on the difference amount between images obtained from the tomographic image data stored in the pre-memory 14.

Next, a virtual period for extracting a plurality of base images is set (S1102). For example, a virtual period may be set to a predetermined initial value. Then, based on the set virtual period, the base image searching unit 24 searches for a plurality of base images from the plurality of sets of tomographic image data stored in the pre-memory 14. Then, based on the base images, the division basis setting unit 26 sets a plurality of division bases, and as described with reference to FIGS. 6 and 8, the reconfiguration process is carried out and an image string after the reconfiguration is stored in the post-memory 28 (S1103).

It should be noted that from S1102 to S1103, the base image searching unit 24 may search for the base images through the process described with reference to FIG. 5, or simply search for the base images at an interval of the virtual period from the plurality of tomographic image data.

When the reconfiguration process has been carried out, a reference image as shown in FIG. 10 is formed by the reference image forming unit 30 (S1104), and the user looks at the reference image to evaluate the distortion (S1105). If the user determines that the distortion is large (NG), the user uses the operation device 21 to modify the virtual period, and the virtual period setting unit 22 sets the modified virtual period (S1102). Then, the processes from S1102 to S1104 are repeated again, and the user looks at the reference image to evaluate the distortion (S1105).

When the processes from S1102 to S1105 are repeated and if the user determines that the distortion is small (OK) at S1105, the base image searching unit 24 uses the modified virtual period to search for a plurality of base images (amended base images) (S1106). At S1106, it is desirable that the base image searching unit 24 searches for base images through the process described with reference to FIG. 5.

When the positions of the base images are amended, the division basis setting unit 26 sets a plurality of division bases based on the amended base images, and the reconfiguration process is carried out as described with reference to FIGS. 6 and 8 (S1107), and the three-dimensional image forming unit 34 forms a reconfigured image based on the image string after the reconfiguration, and displays the reconfigured image on the display unit 36 (S1108). In this way, the reconfigured image, in which the distortion is reduced or completely removed, is displayed.

Turning back to FIG. 1, the object in the present embodiment is tissue in periodic motion or a fluent material which varies on a periodic basis, such as the heart of a fetus or blood flowing through blood vessels of a fetus. If the object is a fluent material such as blood, the tomographic image forming unit 13 forms a tissue image equivalent to a B-mode image based on the echo intensity (magnitude of the echo) obtained from echo data, and also forms a Doppler image such as color Doppler based on Doppler information obtained from the echo data.

Figure 12:
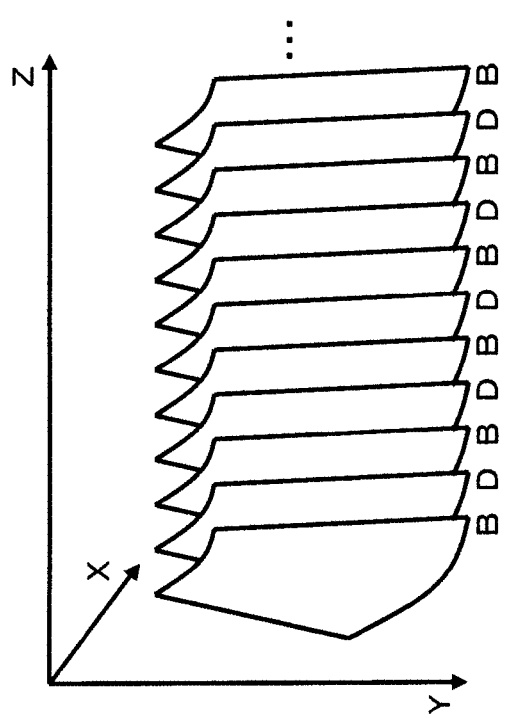
FIG. 12 is an illustration for explaining three-dimensional scanning when Doppler images are included.

FIG. 12 is an illustration for explaining three-dimensional scanning in the case of including Doppler images. In FIG. 12, a three-dimensional region containing an object is expressed in an X-Y-Z Cartesian coordinate system. Even in the case of including Doppler images, a scanning plane is formed so as to be almost in parallel to the X-Y plane, and by gradually displacing the scanning plane in the Z-axis direction, a plurality of scanning planes are formed along the Z-axis direction. For example, if the object is blood of a fetus, the scanning plane is gradually displaced in the Z-axis direction for a time period including about 20 heartbeats in about eight seconds, for example, over a plurality of periods of the periodic motion of the heart of the fetus, for example.

Then, in FIG. 12, a scanning plane B corresponding to a tissue image and a scanning plane D corresponding to a Doppler image are formed alternately along the Z-axis direction. It should be noted that the order of the scanning plane B and the scanning plane D may be changed appropriately such that a plurality of scanning planes B and one scanning plane D are formed alternately, for example.

Turning back to FIG. 1, when a plurality of scanning planes are formed along the Z-axis direction over a plurality of periods of the heartbeats of the fetus, the tomographic image forming unit 13 forms tomographic images for the respective scanning planes, and sets of data of a plurality of tomographic images according to the scanning planes are sequentially stored in the pre-memory 14, as described above. As such, data of tomographic images including tissue images and Doppler images are stored in the pre-memory 14.

Even in the case of including the Doppler images, the error determination unit 16 may determine whether or not the plurality of sets of tomographic image data are favorable, based on the difference amount between the images obtained from the plurality of sets of tomographic image data using Equation 1 (described above).

The virtual period setting unit 22 calculates a virtual period based on the plurality of sets of tomographic image data stored in the pre-memory 14. The virtual period setting unit 22 calculates a virtual period of the tissue image from the tomographic image data relating to the tissue image, and calculates a virtual period of the Doppler image from the tomographic image data relating to the Doppler image. When calculating the respective virtual periods, the virtual period setting unit 22 uses the mutual difference value defined by Equation 2 (described above).

As such, the virtual period setting unit 22 calculates a mutual difference value using Equation 2 with reference to a plurality of sets of tomographic image data relating to the tissue image, and obtains a virtual period of the tissue image from the changes (see FIG. 4) in the calculated mutual difference value. Also, the virtual period setting unit 22 calculates a mutual difference value using Equation 2 with respect to a plurality of sets of tomographic image data relating to the Doppler image, and obtains a virtual period of the Doppler image from the changes in the calculated mutual difference value. In the case of the tissue image, a pixel value p in Equation 2 represents a magnitude (intensity) of the echo data, for example, and in the case of the Doppler image, a pixel value p in Equation 2 represents a Doppler shift amount (velocity value), for example.

Further, the virtual period setting unit 22 may set the identical virtual period (shared virtual period) with respect to the tissue image and the Doppler image. For example, the virtual period setting unit 22 may calculate only a virtual period of the tissue image obtained from the mutual difference value of the tissue image, and set the virtual period of the tissue image as a shared virtual period. Of course, the virtual period setting unit 22 may calculate only a virtual period of the Doppler image obtained from the changes in the mutual difference value of the Doppler image and set the virtual period of the Doppler image as a shared virtual period. Alternatively, a user may input a value of a shared virtual period.

When the virtual period is set, the base image searching unit 24 searches for base images from tomographic image data using the virtual period. The base image searching unit 24 searches for tissue base images from the tomographic image data relating to the tissue images, and searches for Doppler base images from tomographic image data relating to the Doppler images.

As such, the base image searching unit 24 searches for tissue base images by performing the processes shown in FIG. 5 on the tomographic images relating to the tissue images using the tissue virtual period. The base image searching unit 24 also searches for Doppler base images by performing the processes shown in FIG. 5 on the tomographic images relating to the Doppler images using the virtual period of the Doppler image. If a shared virtual image is set, the base image searching unit 24 searches for tissue base images using the shared virtual period, and searches for Doppler base images using the same shared virtual period.

Further, the base image searching unit 24 sets a plurality of base images based on the tissue base images and the Doppler base images.

Figure 13A:
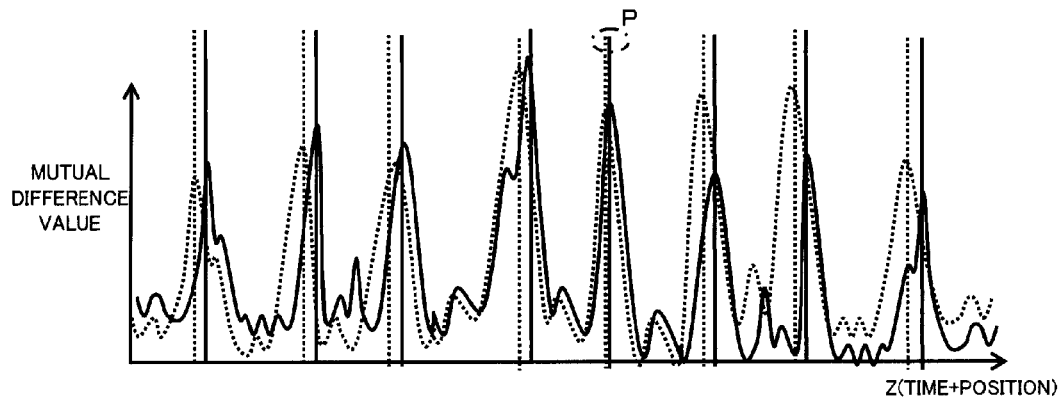
FIG. 13 shows graphs for explaining setting of base images.
Figure 13B:
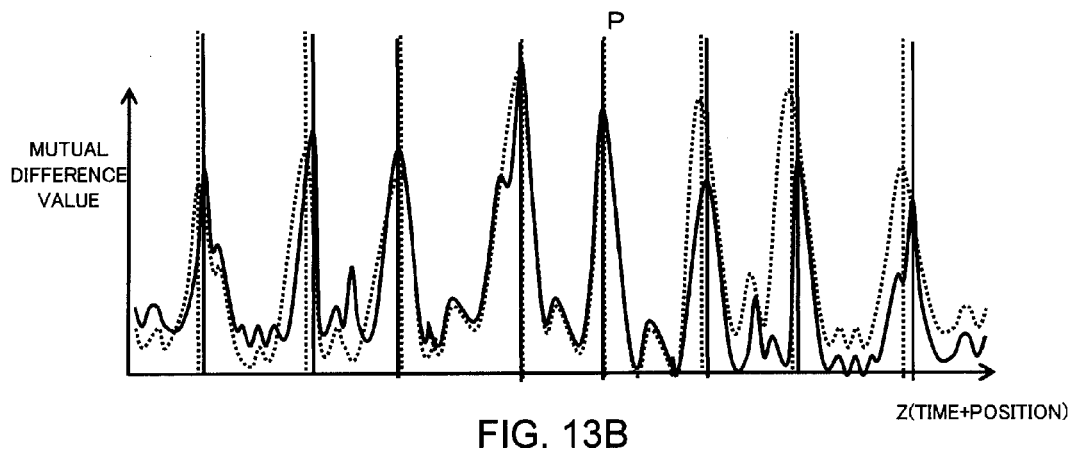
Figure 13C:
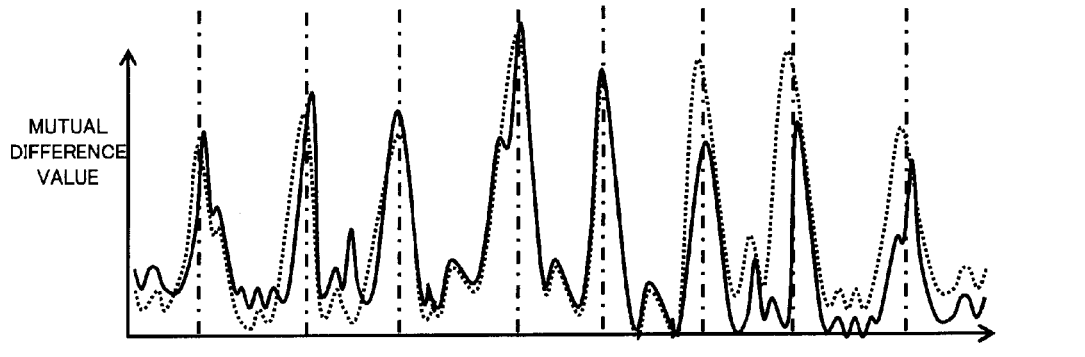

FIG. 13 shows graphs for explaining setting of base images. FIGS. 13(A) to 13(C) respectively show changes (solid-line waveforms) in the mutual difference value of the tissue image and changes (dotted-line waveforms) in the mutual difference value of the Doppler image. Also, FIGS. 13(A) to 13(C) respectively show a plurality of tissue base images (solid lines) and a plurality of Doppler base images (dotted lines).

The base image searching unit 24 first detects, among adjacent tissue base images and Doppler base images, a pair consisting of a tissue base image and a Doppler base image which are closest to each other. Thereby, in the example of FIG. 13(A), a tissue base image and a Doppler base image at a position P are detected.

Then, the base image searching unit 24 displaces all of the Doppler base images along the Z-axis direction while maintaining the distances between each other such that the detected tissue base image and the Doppler base image at the position P overlap each other. FIG. 13(B) shows a state where all of the Doppler base images have been displaced, in which the tissue base image (solid straight line) and the Doppler base image (dotted straight line) at the position P overlap each other. Instead of moving all Doppler base images, all tissue base images may be displaced, or all tissue base images and all Doppler base images may be displaced, such that the tissue base image and the Doppler base image at the position P overlap each other.

Then, the base image searching unit 24 sets intermediate positions between the respective tissue base images and the respective Doppler images, which are adjacent to each other after the displacement, as base images. This means that in FIG. 13(B), an intermediate position between a tissue base image (solid straight line) and a Doppler base image (dotted straight line), which are adjacent to each other, is set as a base image. Thereby, a plurality of base images (dot-dashed straight lines) shown in FIG. 13(C) are determined. It should be noted that at the position P in FIG. 13(B), as the tissue base image and the Doppler base image overlap each other, a base image is set at the overlapped position.

Turning back to FIG. 1, when the base images are searched for, the division basis setting unit 26 sets a plurality of division bases according to the base images within the image string constituted of a plurality of tomographic images (data). As described above, the division basis setting unit 26 uses the respective base images as division bases, for example. Alternatively, as described with reference to FIG. 7, the division basis setting unit 26 sets a plurality of division bases at locations distant from the respective base images by a specified interval.

When the division bases have been set, the reconfiguration processing unit 20 divides the image string into a plurality of image groups using the respective division bases as boundaries for the division. Then, the reconfiguration processing unit 20 extracts from the image groups a plurality of tomographic images which correspond to one another on a periodic basis, to thereby realize a reconfiguration process (reconstruction process). The reconfiguration processing unit 20 reconfigures the tomographic image data stored in the pre-memory 14 and stores them in the post-memory 28, as described with reference to FIGS. 6 and 8.

As described with reference to FIG. 12, in the case where the scanning plane B corresponding to the tissue image and the scanning plane D corresponding to the Doppler image are formed alternately along the Z-axis direction, among the tomographic images Zn stored in the pre-memory 14 shown in FIGS. 6 and 8, the tomographic images for which n is an odd number are tissue images, and the tomographic images for which n is an even number are Doppler images. This means that in the pre-memory 14, the tissue images and the Doppler images are mixed, and the respective tissue images and the respective Doppler images are stored alternately, for example. It should be noted that in the process described with reference to FIG. 13(B), although the Doppler base images have been displaced, the arrangement of the tomographic images stored in the pre-memory 14 is that before the displacement.

Once the reconfiguration processing unit 20 performs processing to reconfigure the image string in which the tissue images and the Doppler images are mixed, and stores them in the post-memory 28, the image string after the reconfiguration process is used in the respective units after the post-memory 28. For example, the three-dimensional image forming unit 34 forms three-dimensional image data for respective time phases by applying various methods such as a volume rendering method, an integration method, or a projection method. In the volume rendering method, a plurality of rays are set with respect to a three-dimensional data region configured of a plurality of sets of tomographic image data constituting one data block, and a volume rendering operation is performed for each of the rays. At that time, an operation performed on the data of the tissue image and an operation performed on the data of the Doppler image on each ray are carried out separately. Then, based on the operational result regarding the tissue image and the operational result regarding the Doppler image on each ray, the final operation result of the ray is calculated.

In this way, the three-dimensional image forming unit 34 forms image data (three-dimensional image data) showing the flow rate information of a fluent material obtained based on the Doppler images within the image expressing the tissue three-dimensionally. Then, the image corresponding to the three-dimensional image data formed over a plurality of time phases is displayed on the display unit 36, and a pseudo three-dimensional moving image is displayed on a real-time basis. For example, images corresponding to three-dimensional image data in a plurality of time phases may be displayed repeatedly to perform loop reproduction.

According to the above embodiment, as a plurality of base images are set based on the tissue base images and the Doppler base images, and the data block is reconfigured based on the base images, even in the case of diagnosing the heart of a fetus, in which the period of heartbeat is unstable, for example, disturbances in the image due to variations of the period are reduced (desirably, completely removed), whereby a highly reliable display image can be acquired.

It is also acceptable to set a plurality of base images using only the Doppler base images without using the tissue base images. For example, Doppler base images may be directly used as the base images.

Further, when forming a display image over a plurality of time phases, the three-dimensional image forming unit 34 may form an image in which flow rate information which can be obtained over the respective time phases is displayed at once.

Figure 14:
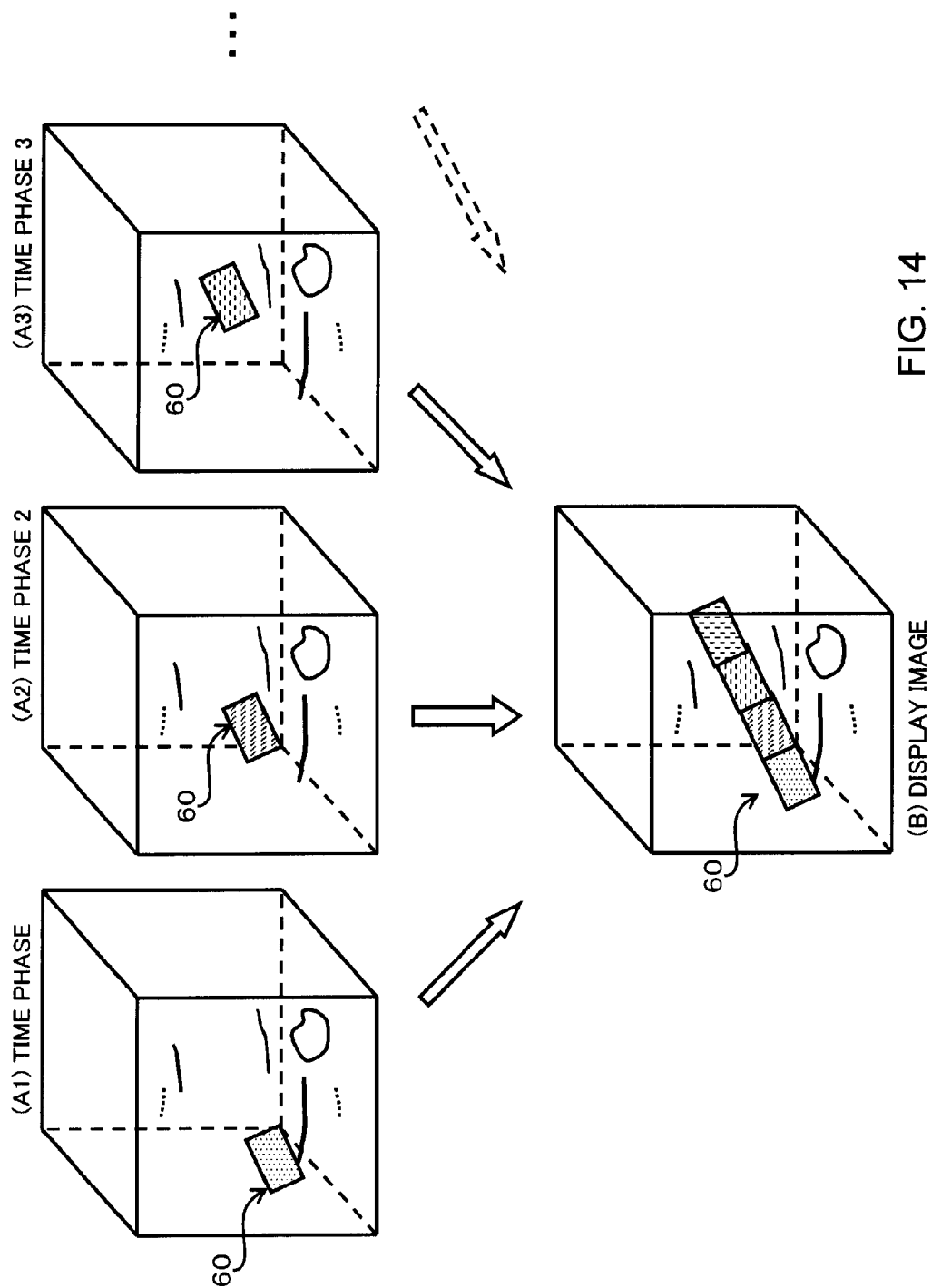
FIG. 14 is an illustration for explaining images showing a plurality of sets of flow rate information over a plurality of time phases.

FIG. 14 is an illustration for explaining an image showing a plurality of flow rate information over a plurality of time phases. (A1) to (A3) in FIG. 14 show images corresponding to three-dimensional image data formed over a plurality of time phases. For example, (A1) shows an image corresponding to three-dimensional image data at a time phase 1, and (A2) shows an image corresponding to three-dimensional image data at a time phase 2. In each of the images shown in (A1) to (A3), flow rate information 60 of a fluent material is displayed on the image showing the tissue three-dimensionally. The flow rate information 60 is an image portion formed based on a Doppler image, and is an image portion which is colored according to the flow rate of the fluent material at that position, for example. As such, portions having different flow rates are indicated in different colors. In FIG. 14, different filling patterns regarding the flow rate information 60, rather than different colors, indicate different flow rates. Of course, in an actual ultrasound image, different patterns as shown in FIG. 14 may be used instead of different colors.

As a display image over a plurality of time phases, although a moving picture showing the respective images in the respective time phases in the order of (A1) to (A3) may be provided, it is also acceptable to form a display image in which a plurality of sets of the flow rate information 60 obtained in the respective time phases are collectively shown.

The illustration (B) in FIG. 14 shows a display image showing a plurality of sets of flow rate information 60 in the respective time phases at once (together). As such, in the illustration (B), a plurality of sets of flow rate information 60 corresponding to (A1) to (A3) and the subsequent time phase are collectively shown together. For example, flow rate information 60 in the entire time phases may be displayed in an overlapped manner according to a logical OR condition. It is desirable that a portion based on the tissue image other than the flow rate information 60 should be displayed for each of the time phases. For example, a portion based on the tissue image other than the flow rate information 60 may be formed as a moving image showing an image of each of the phases in the order of (A1) to (A3), and in that moving image, the flow rate information 60 over the respective time phases may be displayed as shown in the illustration (B). Further, the flow rate information 60 of all time phases may be displayed collectively, or the flow rate information 60 of some characteristic time phases may be selected and displayed collectively.

While a preferred embodiment of the present invention has been described above, the above embodiment is only an example in any aspect and does not limit the scope of the present invention.

What is claimed is:

1. An ultrasound diagnostic apparatus comprising:
a probe that emits and receives ultrasonic waves to and from a three-dimensional region including an object in periodic motion; and
a control unit, wherein the control unit is configured to:
control the probe such that a scanning plane is displaced over a plurality of periods of the motion so as to form a plurality of scanning planes within the three-dimensional region;
set a virtual period which is a temporary period of motion relating to the object;
search for a plurality of base images from an image string constituted of a plurality of images corresponding to the plurality of scanning planes based on a mutual difference value which is a feature amount relating to the periodicity of the motion;
divide the image string into a plurality of image groups using the respective base images as dividing units, and extracts a plurality of images which correspond to one another on a periodic basis from the respective image groups; and form a display image of the object based on the plurality of images which correspond to one another on a periodic basis; wherein
the mutual difference value is calculated for each of the images by multiplying a difference between a pixel value of the image and a pixel value of an adjacent image by one of these two pixel values.

2. The ultrasound diagnostic apparatus comprising:
a probe that emits and receives ultrasonic waves to and from a three-dimensional region including an object in periodic motion; and
a control unit, wherein the control unit is configured to:
control the probe such that a scanning plane is displaced over a plurality of periods of the motion so as to form a plurality of scanning planes within the three-dimensional region;
set a virtual period which is a temporary period of motion relating to the object;
search for a plurality of base images from an image string constituted of a plurality of images corresponding to the plurality of scanning planes based on a mutual difference value which is a feature amount relating to the periodicity of the motion;
divide the image string into a plurality of image groups using the respective base images as dividing units, and extracts a plurality of images which correspond to one another on a periodic basis from the respective image groups; and
form a display image of the object based on the plurality of images which correspond to one another on a periodic basis; wherein
the control unit is configured to calculate the mutual difference value for each of the images by multiplying a difference between a pixel value of the image and a pixel value of an adjacent image by one of these two pixel values, and calculate the virtual period based on intervals between a plurality of images corresponding to a maximum mutual difference value.

3. The ultrasound diagnostic apparatus according to claim 1, wherein
the control unit configured to control the probe so as to acquire a reception signal from a representative portion of the object over the plurality of periods of the motion, and
set a virtual period of the motion of the object based on the reception signal acquired from the representative portion.

4. The ultrasound diagnostic apparatus according to claim 3, wherein
the control unit configured to calculate a feature amount reflecting changes in reception signals between time phases based on the reception signals at a plurality of time phases acquired from the representative portion, and determines the virtual period according to the feature amount.

5. The ultrasound diagnostic apparatus according to claim 1, wherein
the control unit configured to extract images which correspond to one another on a periodic basis from the respective image groups to change the order of the images in the image string to form a reconfigured image string, and
form a reference image indicating a temporal change in the form of the object by the motion, based on the reconfigured image string, and
modify the virtual period according to an instruction from a user who refers to the reference image.

6. The ultrasound diagnostic apparatus according to claim 5, wherein
the control unit configured to form, as the reference image, a tomographic reference image which corresponds to a plane crossing the scanning plane.

7. The ultrasound diagnostic apparatus according to claim 6, wherein
the control unit configured to form the tomographic reference image in which a dilated portion and a contracted portion of the object are shown in different display modes.

8. The ultrasound diagnostic apparatus according to claim 1, wherein
the control unit configured to extract images which correspond to one another on a periodic basis from the respective image groups to change the order of the images in the image string to form a reconfigured image string, and
extract a plurality of images corresponding to the same position from the reconfigured image strings of different time phases, and calculates a difference value between the extracted images.

9. The ultrasound diagnostic apparatus according to claim 1, wherein
the control unit configured to set a plurality of division bases at locations distant from the plurality of base images by a specified interval within the image string, and
divide the image string into a plurality of image groups with the respective division bases serving as boundaries for division.

10. The ultrasound diagnostic apparatus according to claim 9, wherein
the control unit configured to set the specified interval according to an interval between the plurality of base images.

11. The ultrasound diagnostic apparatus according to claim 1, wherein
the control unit configured to search for a plurality of tissue base images from a plurality of tissue images based on echo intensity among a plurality of images constituting the image string and search for a plurality of Doppler base images from a plurality of Doppler images based on Doppler information among the plurality of images constituting the image string, at an interval corresponding to the virtual period, and set the plurality of base images according to the plurality of tissue base images and the Doppler base images.

12. The ultrasound diagnostic apparatus according to claim 11, wherein
the control unit configured to set the base images to be intermediate positions between the respective tissue base images and the respective Doppler base images, wherein the respective tissue base images and the respective Doppler base images are spatially adjacent to each other.

13. The ultrasound diagnostic apparatus according to claim 12, wherein
the control unit configured to set intermediate positions between the respective tissue base images and respective Doppler base images, which are spatially adjacent to each other, as base images after the displacement of at least one of the tissue base images and the Doppler base images such that a tissue base image and a Doppler base image which are closest to each other overlap.

14. An ultrasound diagnostic apparatus comprising:
a probe that emits and receives ultrasonic waves to and from a three-dimensional region including an object in periodic motion; and
means for controlling the probe such that a scanning plane is displaced over a plurality of periods of the motion so as to form a plurality of scanning planes within the three-dimensional region;
means for setting a virtual period which is a temporary period of motion relating to the object;
means for searching a plurality of base images from an image string constituted of a plurality of images corresponding to the plurality of scanning planes based on a mutual difference value which is a feature amount relating to the periodicity of the motion;
means for dividing the image string into a plurality of image groups using the respective base images as dividing units, and extracts a plurality of images which correspond to one another on a periodic basis from the respective image groups; and
means for forming a display image of the object based on the plurality of images which correspond to one another on a periodic basis, wherein
the mutual difference value is calculated for each of the images by multiplying a difference between a pixel value of the image and a pixel value of an adjacent image by one of these two pixel values.

15. The ultrasound diagnostic comprising:
a probe that emits and receives ultrasonic waves to and from a three-dimensional region including an object in periodic motion; and
means for controlling the probe such that a scanning plane is displaced over a plurality of periods of the motion so as to form a plurality of scanning planes within the three-dimensional region;
means for setting a virtual period which is a temporary period of motion relating to the object;
means for searching a plurality of base images from an image string constituted of a plurality of images corresponding to the plurality of scanning planes based on a mutual difference value which is a feature amount relating to the periodicity of the motion;
means for dividing the image string into a plurality of image groups using the respective base images as dividing units, and extracts a plurality of images which correspond to one another on a periodic basis from the respective image groups;
means for forming a display image of the object based on the plurality of images which correspond to one another on a periodic basis; and
means for calculating the mutual difference value for each of the images by multiplying a difference between a pixel value of the image and a pixel value of an adjacent image by one of these two pixel values, and calculating the virtual period based on intervals between a plurality of images corresponding to a maximum mutual difference value.

16. The ultrasound diagnostic apparatus according to claim 14, wherein
means for controlling the probe so as to acquire a reception signal from a representative portion of the object over the plurality of periods of the motion, and
setting a virtual period of the motion of the object based on the reception signal acquired from the representative portion.

17. The ultrasound diagnostic apparatus according to claim 16, wherein
means for calculating a feature amount reflecting changes in reception signals between time phases based on the reception signals at a plurality of time phases acquired from the representative portion, and determines the virtual period according to the feature amount.

18. The ultrasound diagnostic apparatus according to claim 14, wherein
means for extracting images which correspond to one another on a periodic basis from the respective image groups to change the order of the images in the image string to form a reconfigured image string, and
forming a reference image indicating a temporal change in the form of the object by the motion, based on the reconfigured image string, and
modifying the virtual period according to an instruction from a user who refers to the reference image.

19. The ultrasound diagnostic apparatus according to claim 18, wherein
means for forming, as the reference image, a tomographic reference image which corresponds to a plane crossing the scanning plane.

20. The ultrasound diagnostic apparatus according to claim 19, wherein
means for forming the tomographic reference image in which a dilated portion and a contracted portion of the object are shown in different display modes.

21. The ultrasound diagnostic apparatus according to claim 14, wherein
means for extracting images which correspond to one another on a periodic basis from the respective image groups to change the order of the images in the image string to form a reconfigured image string, and
extracting a plurality of images corresponding to the same position from the reconfigured image strings of different time phases, and calculates a difference value between the extracted images.

22. The ultrasound diagnostic apparatus according to claim 14, wherein
means for setting a plurality of division bases at locations distant from the plurality of base images by a specified interval within the image string, and
dividing the image string into a plurality of image groups with the respective division bases serving as boundaries for division.

23. The ultrasound diagnostic apparatus according to claim 22, wherein
means for setting the specified interval according to an interval between the plurality of base images.

24. The ultrasound diagnostic apparatus according to claim 14, wherein
means for searching a plurality of tissue base images from a plurality of tissue images based on echo intensity among a plurality of images constituting the image string and searching a plurality of Doppler base images from a plurality of Doppler images based on Doppler information among the plurality of images constituting the image string, at an interval corresponding to the virtual period, and setting the plurality of base images according to the plurality of tissue base images and the Doppler base images.

25. The ultrasound diagnostic apparatus according to claim 24, wherein means for setting the base images to be intermediate positions between the respective tissue base images and the respective Doppler base images, wherein the respective tissue base images and the respective Doppler base images are spatially adjacent to each other.

26. The ultrasound diagnostic apparatus according to claim 25, wherein means for setting intermediate positions between the respective tissue base images and respective Doppler base images, which are spatially adjacent to each other, as base images after the displacement of at least one of the tissue base images and the Doppler base images such that a tissue base image and a Doppler base image which are closest to each other overlap.

* * * * *